United States Patent [19]
Page et al.

[11] Patent Number: 5,871,920
[45] Date of Patent: Feb. 16, 1999

[54] DAZ: A GENE ASSOCIATED WITH AZOOSPERMIA

[75] Inventors: David C. Page, Winchester; Renee Reijo, Allston, both of Mass.

[73] Assignee: Whitehead Institute for Biomedical Research, Cambridge, Mass.

[21] Appl. No.: 690,734

[22] Filed: Jul. 31, 1996

Related U.S. Application Data

[63] Continuation-in-part of Ser. No. 310,429, Sep. 22, 1994, Pat. No. 5,695,935.
[51] Int. Cl.⁶ .............................. C12Q 1/68; C12P 19/34; C07H 21/02; C07H 21/04
[52] U.S. Cl. .......................... 435/6; 435/91.1; 435/91.2; 536/23.1; 536/24.3; 536/24.33
[58] Field of Search ............................. 435/6, 91.1, 91.2; 536/23.1, 24.3, 24.33; 530/300, 350

[56] References Cited

PUBLICATIONS

Glaser et al. Chromosome Research 5: 23–30, 1997.
Yen et al. Am J. of Human Genetics 57; A876, 1995.
Reijo et al. Nature Genetics 10:383–393, 1995.
Foote et al. Science 258: 60–66, 1992.

Ma, Kun et al., "A Y Chromosome Gene Family with RNA–Binding Protein Homology: Candidates for the Azoospermia Factor AZF Controlling Human Spermatogenesis", *Cell* 75:1287–1295 (1993).

Foote, Simon et al., "The Human Y Chromosome: Overlapping DNA Clones Spanning the Euchromatic Region", *Science* 258:60–66 (1992).

Vollrath, Douglas et al., "The Human Y Chromosome: A 43–Interval Map Based on Naturally Occurring Deletions", *Science* 258:52–59 (1992).

*Primary Examiner*—W. Gary Jones
*Assistant Examiner*—Dianne Rees
*Attorney, Agent, or Firm*—Hamilton, Brook, Smith & Reynolds, P.C.

[57] ABSTRACT

Novel gene present in interval 6E of the distal portion of the long arm of the human Y chromosome, whose alteration is associated with reduced sperm count. Methods of diagnosis and treatment utilizing said gene, and antibodies that bind to the protein encoded by said gene.

10 Claims, 22 Drawing Sheets

3/1
TCA GCT GGG GTC TAC TCC GAG GGT TCG CCC GAC CTT GGT TTT CCT TAC ACC TTA GCC TTT GGC TCC TTG ACC ACT CGA GCC CCA CAG GTG
                                                                33/11                                    63/21

93/31
TTC CAG CGG ACT TCA CCA GCA GAC CCA GAA GTG GGT GAA ACA CTG CCT GTC CTC TTC CTT GAG CCT GTC GGG AGC TGC TGC CTG CCA
       123/41                                                            153/51

183/61
CCA CCA TGT CTG CTG CAA ATC CTG AGA CTC CAA ACT CAA CCA GCA CCC AGT CTT CAT CAG CTG CAG CTA GCC AAG
       213/71                                                        243/81

273/91
GCT GGG TGT TAC CAG AAG GCA AAA TCG TGC CAA ACA CTG TTT TTT GTT GGT GGA ATT GAT GCT AGG ATG GAT GAA ACT GAG ATT GGA AGC
       303/101                                                                333/111

363/121
TGC TTT GGT AGA TAC GGT TCA GTG AAA AGA AGT GAA GAT AAT CAC GAA TCG AAC TGG TGT TCC AAA GGC TAT GGA TTT GTT TCG TTT GTT
       393/131                                                                    423/141

453/151
AAT GAC GTG GAT GTC CAG AAG ATT AGT AGG ATC ACA GAA TAC ATC TCC ATG GGT AAA AAG CTG AAG CTG GGC CCT GCA ATC AGG AAA CAA
       483/161                                                                        513/171

543/181
AAG TTA TGT GCT CGT CAT GTG CAG CCA CGT CCT TTG GTA GTT AAT CCT CCT CCA CCA CAG TTT CAG AAC GTC TGG CGG AAT CCA AAC
       573/191                                                                603/201

633/211
ACT GAA ACC TAC CTG CAG CCC CAA ATC ACG CCG AAT CCT GTA ACT CAG TAC GTT CAG TCT GCT GCA AAT CCT
       663/221                                      693/231

FIG. 1

GAGTAATCAXATGCAXGTCATACTGAATTTGTACTGTATCACAGGTACTTCTTG

GAGAAGTGAAATGCTTGTGTTCAGACTATCAAAATTGTTAGCTTACAAATCAGG

TTTTAAAAACTTTTGGAAAGTCAGTATGTGCTTTTAAACACTTAAATGCAXGTC

TCAXTTTTTTTTTTTTTCCGXAGATATCTTAACATTCTTCAGTCTCGATTATGTG

TTACTTTAAACTATATATTAAACACAGACCCAGGTTCTAAATAAACATCTAATG

AAGAACAGCATCGTTAAGATAAAAACTAGAGAGTCTAATAATACAAGTTATAC

AGAAAGTTTCAGTGTGATTTCCAAATTCAGAATTTCAGTAATAGTGGAAAAACT

TTTAGCTTATATCACCCAGCACTCCCCATGAAACTAGATGCTGAGAGGCC

| PATIENT NO. | Category |
|---|---|
| 2475 | Terminal Deletion |
| 1305 | Terminal Deletion |
| 1310 | Terminal Deletion |
| 1318 | Terminal Deletion |
| 2064 | Terminal Deletion |
| 746 | Terminal Deletion |
| 1788 | Terminal Deletion |
| 2240 | Terminal Deletion |
| 2168 | Terminal Deletion |
| 496 | Terminal Deletion |
| 2229 | Terminal Deletion |
| 1078 | Terminal Deletion |
| 1659 | Normal, Fertile |
| 2376 | Infertile |
| 2381 | Infertile |
| 2415 | Infertile |
| 2430 | Infertile |
| 2613 | Infertile |
| 2615 | Infertile |
| 2564 | Infertile |
| KLARD | Infertile |
| KUPAU | Infertile |
| MKB | Infertile |

```
                                                              AGTCGGCCTGCG

CTCC-TCAGCCTGGCGGTTCTACCTCCGAGGGTTCGCCCGCCCTTGGTTTTCCTTACACC

TTAGCCTTTGGCTCCTTTGACCACTCGAAGCCCCACAGCGTGTTCCAGCGGACTTCACCA

GCAGACCCAGAAGTGGTGGGTGAAACACTGCCTCTGTTCCTCCTTGAGCCTGTCGGGAGC

TGCTGCCTG---------------CCACCACCATGTCTGCTGCAAATCCTGAGACTCC

AAACTCAACCATCTCCAGAGAGGCCAGCACCCAGTCTTCATCAGCTGCAGCTAGCCAAGG

CTGGGTGTTACCAGAAGGCAAAATCGTGCCAAACACTGTTTTT--GTTGGTGGAATTGAT

GCTAGGATGGATGAAACTGAGATTGGAAGCTGCTTTGGTAGATACGGTTCAGTGAAA-GA

AGTGAAGATAATCACGAATCGAACTGGTGTGTCCAAAGGCTATGGATTTGTTTCGTTTGT

TAATGACGTGGATGTCCAGAA-GAT-AGTAGGA-TCACAGA-TACATTTCCAT-GGTAAA
```

Figure 4A

AGAGACTGATAAATTCCGTTGTTACTCAAGATGACTGCTTCAAGGGTAAAAGAGTGCATC

GCTTTAGAAGAAGTTTGGCAGTATTTAAATCTGTT-GGATCCTCTCAGCTATCTAGTTTC

ATGGGAAGTTGCTGGTTTTGAATATTAAGCTAAAAGTTTT-CCACTATTACAGAAATTCT

GAATTTTGGTAAATCACACTGAAACTTTCTGTATAACTTGTATTATTAGACTCTCTAGTT

TT-ATCTTAACACTGAAACTGTTCTTCATTAGATGTTTATTTAGAACCTGGTTCTGTGTT

TAATATATAGTTTAAAGTAACAAATAATCGAGACTGAAAGAATGTTAAGATTTATCTGCA

AGGATTTTTAAAAAATTGAAACTTGCATTTTAAAGTGTTTAAAAGCAAATTACTGACTTT

C-AAAAAAGTTTTTAAAACCTGATTTGAAAGCTAACAATTTTGGATAGTCTGAACACAAG

CATTTCACTTCTCCAAGAAGTACCTGTGA-ACAGTACAATATTTCAGTATTGAGCTTTGC

ATTTATGATTTATC

Figure 4B

AAGCTGAAGCTGGGCCCTGCAATCAGGAAACAAAAGTTATGTGCTCGTCATGTGCAGCCA

CGTCCTTTGGTAGTTAATCCTCCTCCTCCACCACAGTTTCAGAACGTCTGGCGGAATCCA

AACACTGAAACCTACCTGCAGCCCCAAATCACGCCGAATCCTGTAACTCAGCACGTTCAG

GCTTATTCTGCTTATCCACATTCACCAGG-TCAGGTCATCACT-G-GATGTCAGTTGCTT

GTATATAATTATCAGGAA-TATCCTACTTATCCGATTCACCATTTCAGGTCACCACTGG

ATATCAGTTGCCTGTATATAATTATC-AGCCATTTCCTGCTTA-TCCAAGTTCACCATTT

CAGGTCACTGCTGGATATCAGTTGCCTGTATATAATTATCAGGCATTTCCTGCTTATCCA

AGTTCACCATTTCAGGTCACCACTGGATATCAGTTGCCTGTATATAATTATCAGGCATTT

CCTGCTTATCCAAGTTCACCATTTCAGGTCACCACTGGATATCAGTTGCCTGTATATAAT

TATCAGGCATTTCCTGCTTATCCAAGTTCACCATTTCAGGTCACCACTGGATATCAGTTG

CCTGTATATAATTATCAGGCATTTCCTGCTTATCCAAATTCAGCAGTTCAGGTCACCACT

GGATATCAGTTCCATGTATACAATTACCAGATGCCACCGCAGTGCCCTGTTGGGGAGCAA

AGGAGAAATCTGTGGACCGAAGCATACAAATGGTGGTATCTTGTCTGTTTAATCCAGAGA

Figure 4C

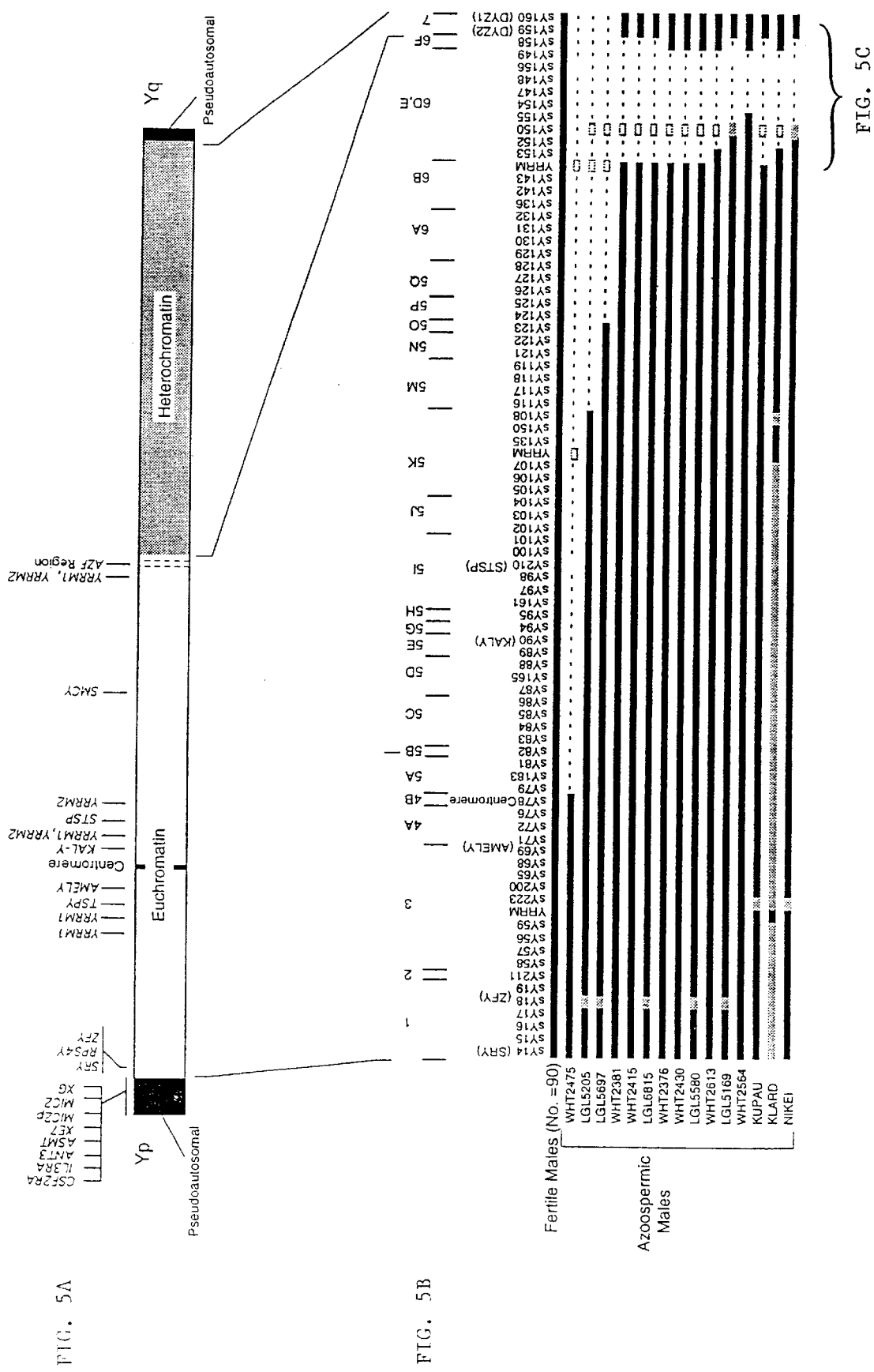

| FIG. 6A | FIG. 6B | FIG. 6C |
| --- | --- | --- |
| FIG. 6D | FIG. 6E | FIG. 6F |
| FIG. 6G | FIG. 6H | FIG. 6I |

FIG. 6J

MSAANPETPNSTISREASTQSSSAAASQGWVLPEGKIVPN

TVFVGGIDARMDETEIGSCFGRYGSVKEVKIITNRTGVSK

GYGFVSFVNDVDVQKIVGSQIHFHGKKLKLGPAIRKQKLC

ARHVQPRPLVVNPPPPQFQNVWRNPNTETYLQPQITPNP

VTQHVQAYSAYPHSPGQNITGCQLLVYNYQEYPTYPDSPF

QVTTGYQLPVYNYQPFPAYPSSPFQVTAGYQLPVYNYQAF

PATPSSPFQVTTGYQLPVYNYQAFPAYPSSPFQVTTGYQL

PVYNYQAFPAYPSSPFQVTTGYQLPVYNYQAFPAYPNSAV

QVTTGYQFHVYNYQMPPQCPVGEQRRNLWTEAYKWWYLVC

LIQRRD

Figure 7

DAZ: A GENE ASSOCIATED WITH AZOOSPERMIA

RELATED APPLICATIONS

This application is a Continuation-in-Part application of U.S. application Ser. No. 08/310,429, filed Sep. 22, 1994, U.S. Pat. No. 5,695,935. The teachings of this prior application are incorporated herein in their entirety.

FUNDING

Work described herein was supported by grant RO1-HGOO257 from the National Institute of Health, National Center for Genome Research, funding from the Howard Hughes Foundation and funding from the Damon Runyon-Walter Winchell Foundation Cancer Research Fund. The United States Government has certain rights in the invention.

BACKGROUND OF THE INVENTION

Male infertility is a concern for many couples. Worldwide studies have shown that 2%–7% of all couples have experienced difficulty in achieving conception or are unable to bear children, especially as they near the end of their reproductive life. (Sara A., *Advances in Fertility and Sterility, Proc. Twelfth World Congress Fer. Steril.* 4:91–92 (1987)). Furthermore, among men who seek help or advice at fertility clinics, slightly more than 10% are diagnosed as having oligospermia or azoospermia of unknown origin. (Hargreave, T. B., *The Management of Male Infertility*, T. B. Hargreave and T. E. Soon, eds. (Singapore: PG Publishing, pp. 2–21, 1990)). At this time, little is known about the causes of reduced spermatogenesis and, although various treatments are available, improved methods are still needed.

SUMMARY OF THE INVENTION

This invention pertains to an isolated gene present in interval 6E of the distal portion of the long arm of the human Y chromosome, whose alteration is associated with reduced sperm count. This gene, which appears to be testis-specific, is approximately 3.1 kb in size, and encodes a protein homologous in certain domains to several RNA binding proteins. This gene is referred to herein as the DAZ gene.

The present invention also relates to a method of diagnosing reduced sperm count associated with alteration of a gene in interval 6E of the distal portion of the long arm of the Y chromosome and particularly to a method of diagnosing reduced sperm count associated with alteration of the DAZ gene. In one embodiment of the present method, deletion of the gene is assessed, such as by a hybridization method in which a nucleotide sequence (nucleic acid sequence) which hybridizes to the gene described herein (or portion of that gene) is used to assess Y chromosome DNA for the presence or absence of the gene. For example, lack of hybridization of the nucleotide sequence used to assess DNA sample obtained from a male who has a reduced sperm count indicates that the gene is deleted and that the reduced sperm count is associated with the deletion. The present invention also relates to nucleotide sequences for use as probes or primers for methods of diagnosing reduced sperm count associated with alteration of the gene described herein.

The present invention further relates to the encoded protein, which includes the amino acid sequence of the RNA binding domains conserved among members of the family of RNA binding proteins. This invention also relates to a method of treating reduced sperm count, such as by a gene therapy method in which the gene described herein, or a gene portion which encodes a functional protein, is introduced into a man whose sperm count is reduced and in whom the gene is expressed and the encoded protein replaces the protein normally produced or enhances the quantity produced.

The novel gene described herein has been designated the DAZ gene, and has been shown to be altered in men whose sperm count is reduced. The complete DAZ cDNA sequence (SEQ ID NO: 15) is shown in FIG. 4. The DAZ gene is located exclusively within the 6E deletion interval, appears to encode a testis-specific transcript, is present in a single copy on the Y chromosome of higher primates, and probably has a homologue in lower mammals. The DAZ gene appears to be part of a small gene family located in the same region of the Y chromosome; there also appears to be a related gene on chromosome 3.

Thus, this invention has application to several areas. It may be used diagnostically to identify males with reduced sperm count in whom the gene has been altered. It may also be used therapeutically in gene therapy treatments to remedy fertility disorders associated with alteration of the gene. The present invention may also be useful in designing or identifying agents which function as a male contraceptive by inducing reduced sperm count. This invention also has application as a research tool, as the nucleotide sequences described herein have been localized to interval 6E of the distal portion of the long arm of the human Y chromosome and can therefore serve as markers for the interval.

BRIEF DESCRIPTION OF THE DRAWINGS

FIG. 1 is a partial nucleotide sequence (SEQ ID NO: 1) of a gene which is a member of the DAZ gene family.

FIG. 2 is a partial nucleotide sequence (SEQ ID NO: 2) of a gene which is a member of the DAZ gene family; the partial sequence represented by SEQ ID NO: 2 is 5' of the partial sequence represented by SEQ ID NO: 1.

FIGS. 3A, 3B, 3C and 3D show a map of patient deletions and YAC clones spanning the entire interval. The numbers proceeded by "yS" along the top margin are sequence-tagged sites (STS). The letters "na" indicate that the site was not analyzed.

FIGS. 4A, 4B and 4C indicate the DAZ cDNA sequence (SEQ ID NO: 15).

FIGS. 5A, 5B and 5C show the chromosomal STSs, both new and previously published, which were tested for in DNA samples from men with reduced sperm count.

Figure 6A:
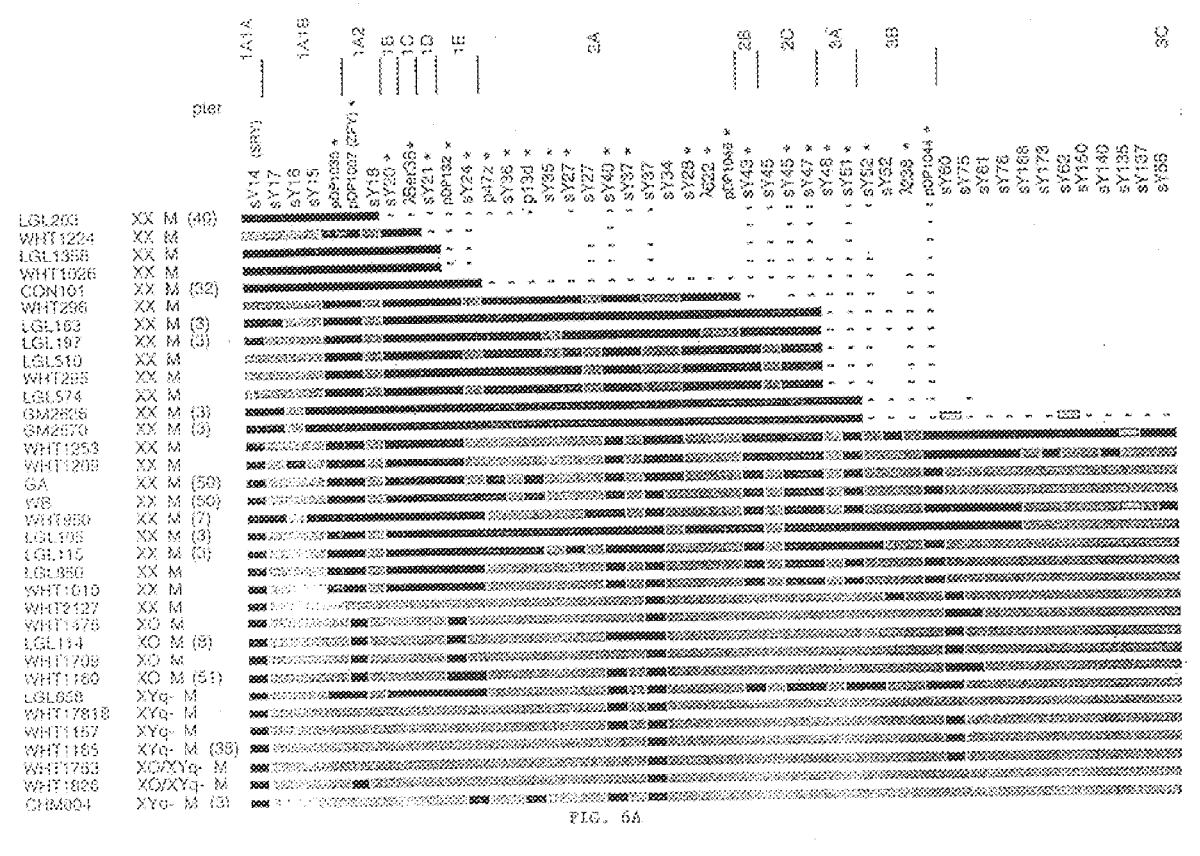
Figure 6D:
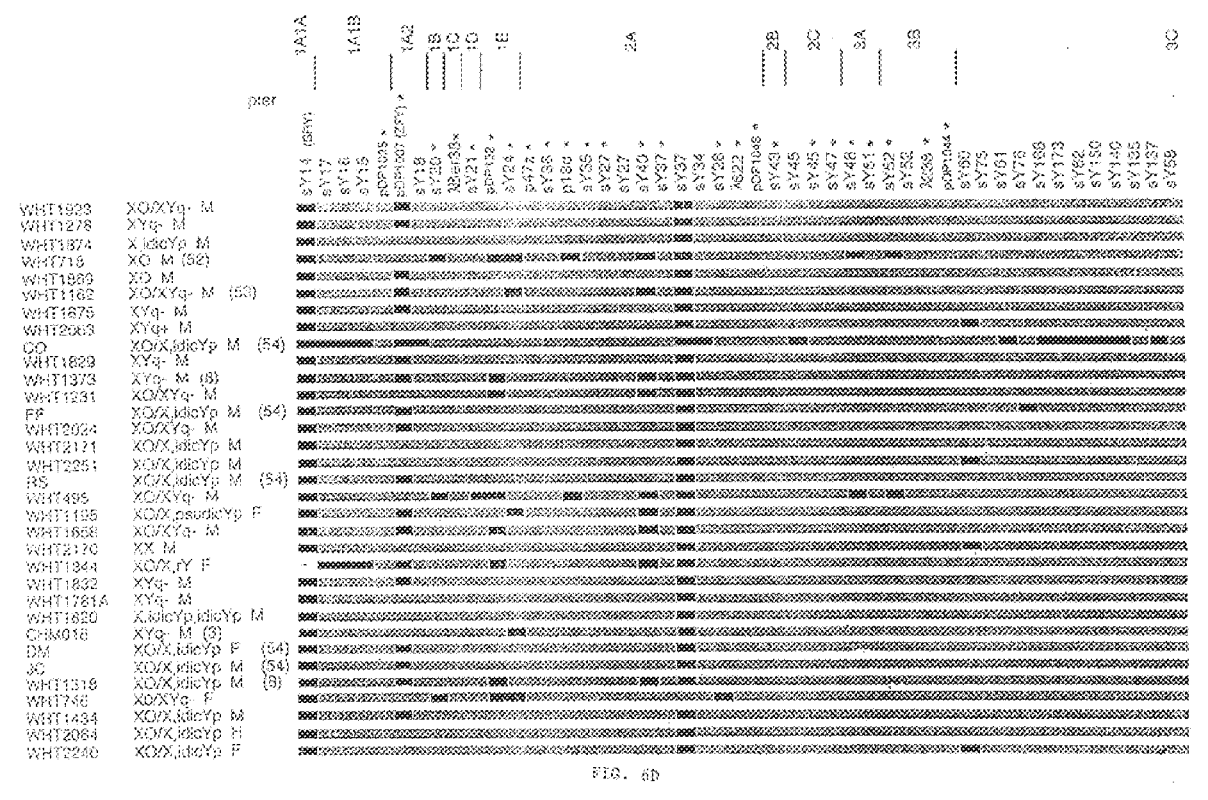
Figure 6F:
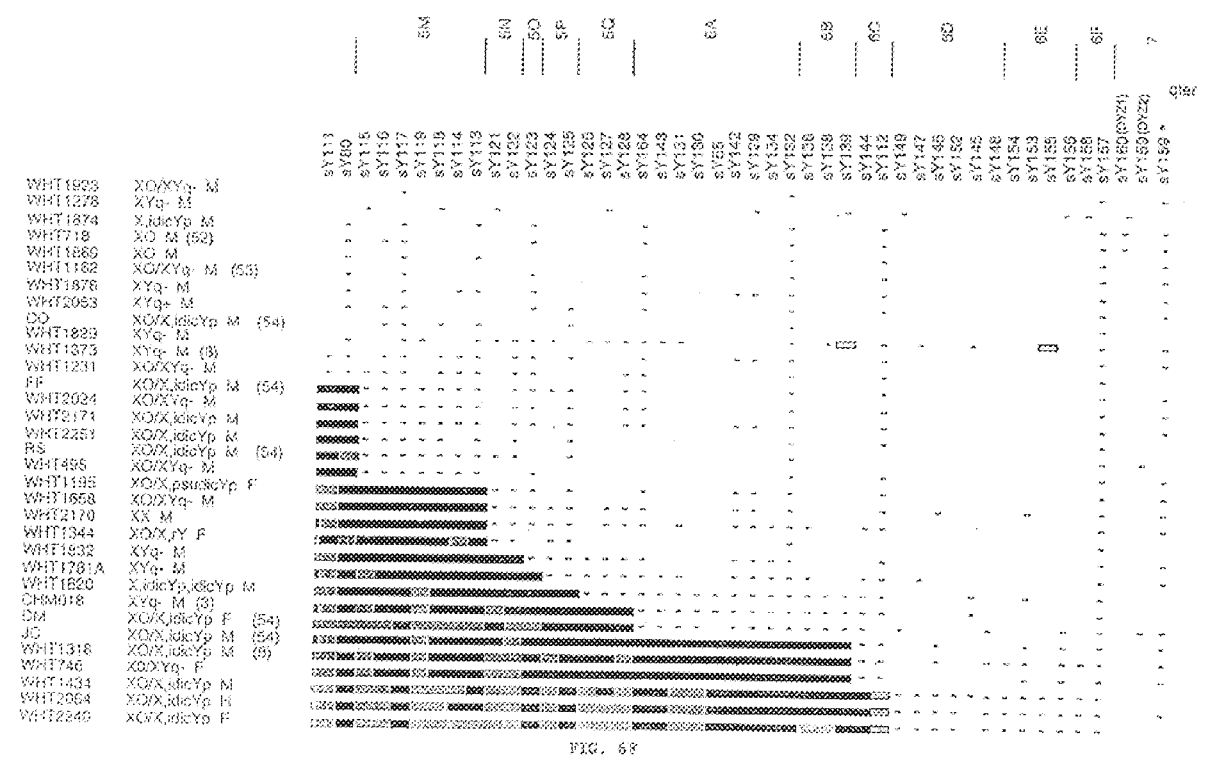

FIGS. 6A through 6J are a 43-interval deletion map of the human Y chromosome taken from Vollrath et al., *Science* 258:52–69 (1992). Along the left border are listed 96 individuals who carry part, but not all, of the Y chromosome (abbreviated karyotypes are given; M, male; F, female; H, hemaphrodite). Along the top margin are listed deletion intervals 1A1A through 7. Listed immediately below the intervals are 132 Y-chromosomal DNA loci comprising 122 STS's and ten unsequenced plasmid or phage clones. The experimentally demonstrated presence of a locus in an individual is indicated by a black segment; the inferred presence (by extrapolation) of a locus in an individual is indicated by a gray segment. Experimentally demonstrated absence is indicated by a minus, and inferred absence is indicated by the absence of any symbol. White boxes represent positive PCR results, and gray boxes represent a few PCR results for repeated or X-Y homologous loci that are positive but of reduced strength relative to results obtained with normal males.

FIG. 7 is the predicted amino acid sequence (SEQ ID NO: 96) of the protein encoded by the DAZ gene.

DETAILED DESCRIPTION OF THE INVENTION

The present invention pertains to a small family of novel genes referred to as the DAZ gene family, present in interval 6E of the distal portion of the long arm of the human Y chromosome, whose alteration is associated with reduced sperm count. As described herein, the Y chromosomes of infertile males, their fathers and normal males have been studied. Among 71 infertile males, 8 males have been identified who have de novo overlapping interstitial deletions on the distal long arm of the Y-chromosome; no such deletions were detected in normal males. The size of the deletion interval which contains this gene, approximately 3.1 kb in size, is approximately 500 kb. The DAZ gene appears to be part of a small gene family (herein termed the DAZ gene family) whose members are located in the same region of the Y chromosome; there also appears to be a related gene on chromosome 3. The gene family members located on the Y chromosome are more than 90 percent identical at the DNA level to the DAZ gene. The gene located on chromosome 3 appears to be 87–94 percent identical at the DNA level to the DAZ gene; the most highly conserved regions exhibit about 94 percent identity. Partial nucleotide sequences of a gene which is a member of the DAZ gene family are shown in FIGS. 1 and 2 (SEQ ID NOS: 1 and 2).

Figures 3, 3A:
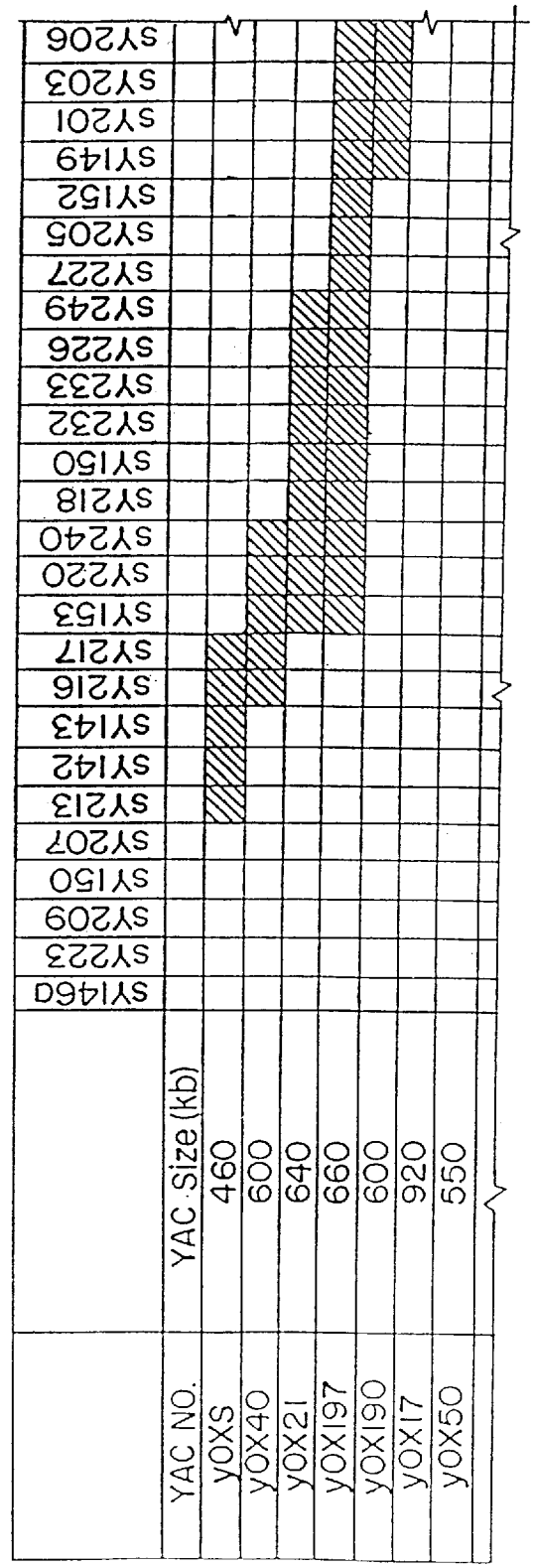
Figure 3B:
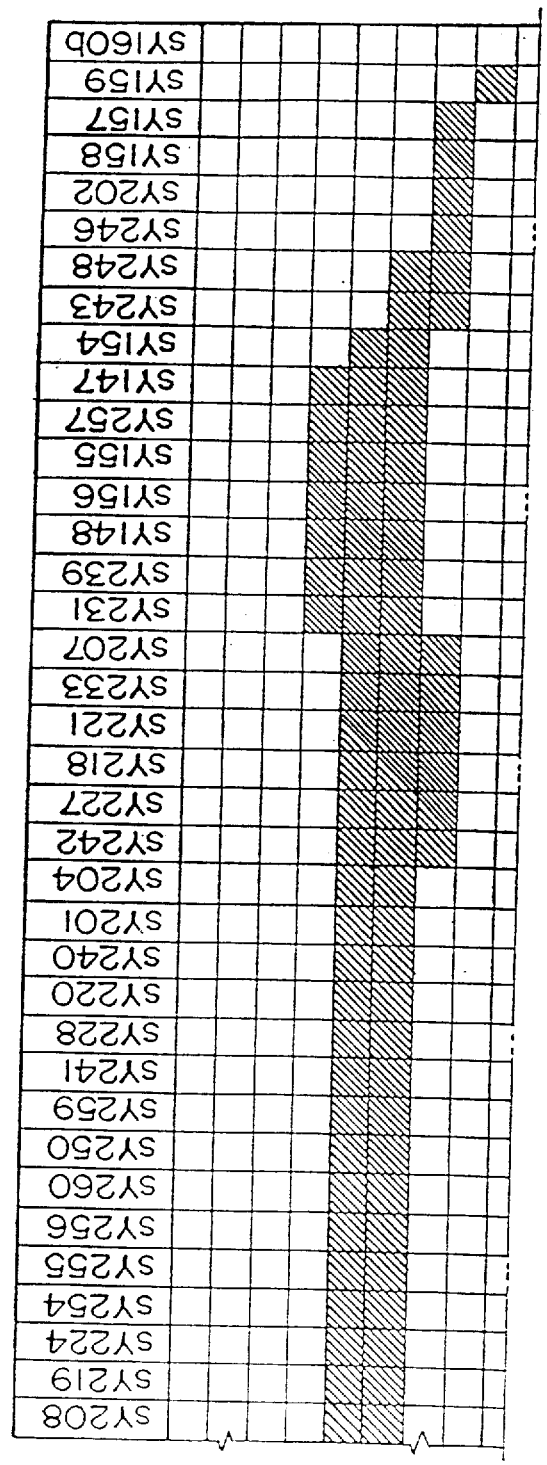
Figure 3D:
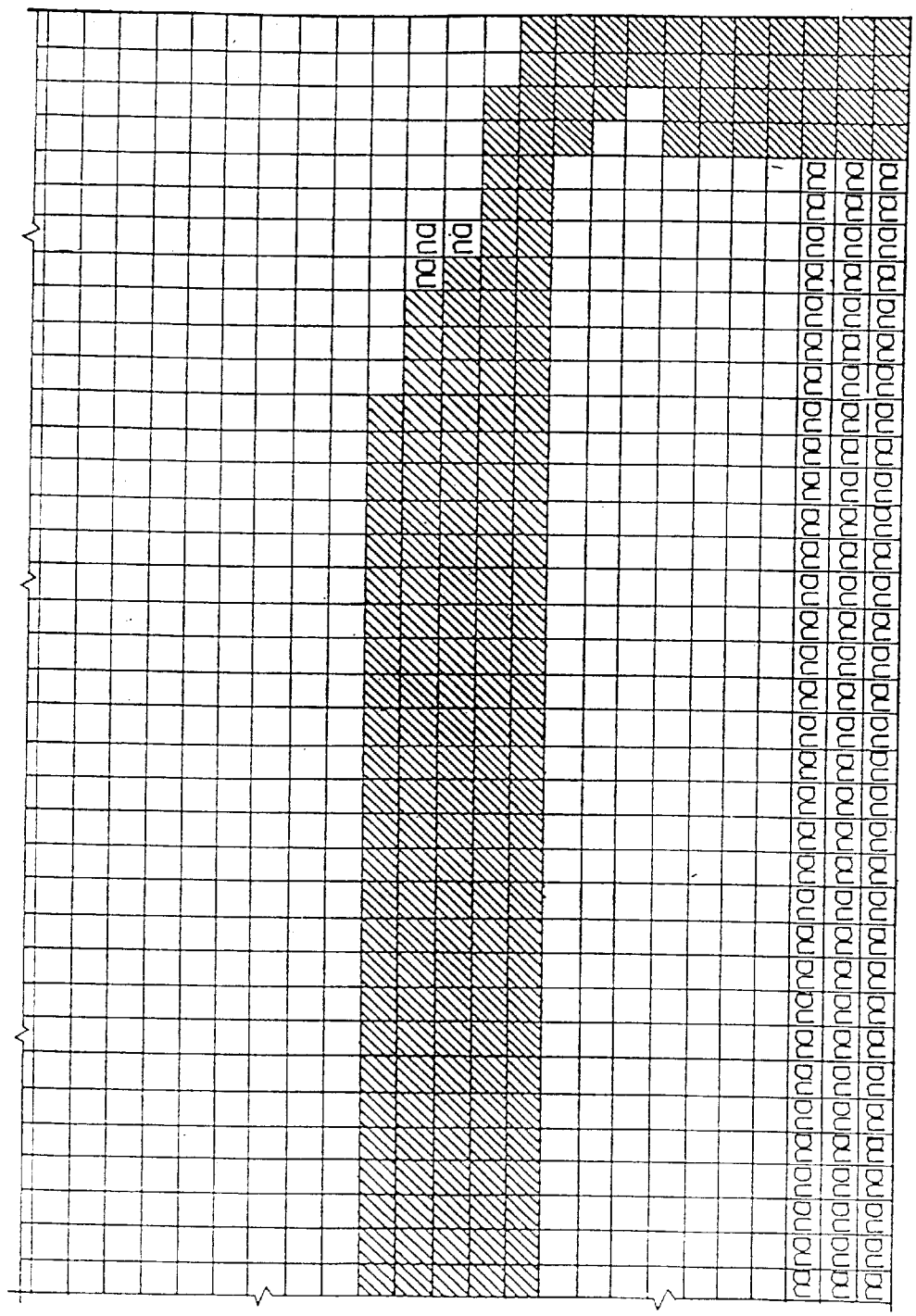

In order to identify the gene whose alteration is associated with reduced sperm count, the relevant deletion interval was analyzed for transcription units by using markers in the deletion interval, identifying yeast artificial chromosomes (YACs) that span the region (see FIG. 3), obtaining 5-fold cosmid coverage of the interval, and using exon-trapping of cosmids to identify sequences with coding potential.

The present invention also pertains to novel methods for diagnosing and treating reduced sperm count associated with an alteration of the gene of the present invention. The present invention also has utility as a research tool, since the gene described herein, or a portion thereof, serves as a marker for the 6E deletion interval of the long arm of the Y chromosome to which it is localized. The cDNA sequence (SEQ ID NO: 15) of the DAZ gene is shown in FIG. 4.

Terms used throughout the Specification are understood to have their art-recognized meaning unless otherwise defined. As used herein, the term "alteration of the gene" includes disruption of the gene (deletion of one or more nucleotides, addition of one or more nucleotides, or change in one or more nucleotides) and loss of the gene. Azoospermia is defined as a condition wherein the concentration of sperm in a semen sample is 0 to occasional sperm per ml, and oligospermia is defined as a condition wherein the concentration of sperm in a semen sample ranges from occasional to less than 20 million per ml. Reduced sperm count is understood to encompass both oligospermia and azoospermia, i.e., a sperm count of less than 20 million per ml, including total absence of sperm. As used herein, an "isolated" gene or nucleotide sequence is intended to mean a gene or nucleotide sequence which is not flanked by DNA sequences which normally (in nature) flank the gene or nucleotide sequence. Thus, an isolated gene or nucleotide sequence can include a gene or nucleotide sequence which is synthesized chemically or by recombinant means.

The gene of the present invention was identified by searching the relevant deletion interval for transcription units by combining additional new markers with known markers over the deletion interval, identifying yeast artificial chromosomes which span the region, obtaining five-fold cosmid coverage of the interval and using exon-trapping of cosmids to identify sequences with coding potential. Once this candidate gene was identified, it was characterized to determine if it fit the profile of a gene whose alteration is associated with reduced sperm count. As described further below, the gene of the present invention is located exclusively within the deletion interval, has a testis-specific transcript and is present in a single copy on the Y chromosome.

The present invention also includes the nucleotide sequences described herein, and their complements, which are useful as hybridization probes or primers for an amplification method, such as polymerase chain reaction (PCR), to show the presence, absence or disruption of the gene of the present invention. Probes and primers can have all or a portion of the nucleotide sequence (nucleic acid sequence) of the gene described herein or all or a portion of its complement. For example, sequences shown in Tables 1, 3 and 4 (SEQ ID NOS: 3–8 and 18–89) can be used, as well as the nucleotide sequence of SEQ ID NO: 15 or its complement. The probes and primers can be any length, provided that they are of sufficient length and appropriate composition (i.e., appropriate nucleotide sequence) to hybridize to all or an identifying or characteristic portion of the gene described or to a disrupted form of the gene, and remain hybridized under the conditions used. Useful probes include, but are not limited to, nucleotide sequences which distinguish between the DAZ gene and an altered form of the DAZ gene shown, as described herein, to be associated with reduced sperm count (azoospermia, oligospermia). Generally, the probe will be at least 7 nucleotides, while the upper limit is the length of the gene itself, e.g., up to about 40,000 nucleotides in length. Probes can be, for example, 10 to 14 nucleotides or longer; the length of a specific probe will be determined by the assay in which it is used.

In one embodiment, the present invention is a method of diagnosing reduced sperm count associated with an alteration in the gene referred to herein as the DAZ gene. Any man may be assessed with this method of diagnosis. In general, the man will have been at least preliminarily assessed, by another method, as having a reduced sperm count. By combining nucleic acid probes derived either from the isolated native sequence or cDNA sequence of the gene, or from the primers disclosed in Table 2, with the DNA from a sample to be assessed, under conditions suitable for hybridization of the probes with unaltered complementary nucleotide sequences in the sample but not with altered complementary nucleotide sequences, it can be determined whether the patient possesses the intact gene. If the gene is unaltered, it may be concluded that the alteration of the gene is not responsible for the reduced sperm count. This invention may also be used in a similar method wherein the hybridization conditions are such that the probes will hybridize only with altered DNA and not with unaltered sequences. The hybridized DNA can also be isolated and sequenced to determine the precise nature of the alteration associated with the reduced sperm count. DNA assessed by the present method can be obtained from a variety of tissues and body fluids, such as blood or semen. In one embodiment, the above methods are carried out on DNA obtained from a blood sample.

The invention also provides expression vectors containing a nucleotide (nucleic acid) sequence present in interval 6E of the distal portion of the long arm of the human Y chromosome, whose alteration is associated with reduced sperm count, and encoding a protein or peptide, which is operably linked to at least one regulatory sequence. "Operably linked" is intended to mean that the nucleotide sequence is linked to a regulatory sequence in a manner which allows expression of the nucleotide sequence. The term "regulatory sequence" includes promoters, enhancers, and other expression control elements (see, e.g., Goeddel, *Gene Expression Technology: Methods in Enzymology* 185, Academic Press, San Diego, Calif. (1990)). It should be understood that the design of the expression vector may depend on such factors as the choice of the host cell to be transformed and/or the protein or peptide desired to be expressed. For instance, the peptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Prokaryotic and eukaryotic host cells transfected by the described vectors are also provided by this invention. For instance, cells which can be transfected with the vectors of the present invention include, but are not limited to, bacterial cells such as *E. coli*, insect cells (baculovirus), yeast and mammalian cells, such as Chinese hamster ovary cells (CHO).

Thus, a nucleotide sequence described herein can be used to produce a recombinant form of the protein via microbial or eukaryotic cellular processes. Production of a recombinant form of the protein can be carried out using known techniques, such as by ligating the oligonucleotide sequence into a DNA or RNA construct, such as an expression vector, and transforming or transfecting the construct into host cells, either eukaryotic (yeast, avian, insect or mammalian) or prokaryotic (bacterial cells). Similar procedures, or modifications thereof, can be employed to prepare recombinant proteins according to the present invention by microbial means or tissue-culture technology.

The present invention also pertains to pharmaceutical compositions comprising the proteins and peptides described herein. For instance, the peptides or proteins of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents.

This invention also has utility in methods of treating disorders of reduced sperm count associated with alteration of the gene. It may be used in a method of gene therapy, whereby the gene or a gene portion encoding a functional protein is inserted into cells in which the functional protein is expressed and from which it is generally secreted to remedy the deficiency caused by the defect in the native gene.

The invention described herein also has application to the area of male contraceptives, since alteration of the DAZ gene produces the functional effects which are desirable in a male contraceptive, e.g., failure to produce sperm without other apparent physiological consequences. Thus, the present invention also relates to agents or drugs, such as, but not limited to, peptides or small organic molecules which mimic the activity of the altered DAZ gene product. Alternatively, the agent or drug is one which blocks or inhibits the activity or function of the unaltered DAZ gene (e.g., an oligonucleotide or a peptide). The ideal agent must enter the cell, in which it will block or inhibit the function of the DAZ gene, directly or indirectly.

The present invention is also related to antibodies which bind a protein or peptide encoded by all or a portion of the intact gene, as well as antibodies which bind the protein or peptide encoded by all or a portion of a disrupted form of the gene. For instance, polyclonal and monoclonal antibodies which bind to the described polypeptide or protein are within the scope of the invention. A mammal, such as a mouse, hamster or rabbit, can be immunized with an immunogenic form of the protein or peptide (an antigenic fragment of the protein or peptide which is capable of eliciting an antibody response). Techniques for conferring immunogenicity on a protein or peptide include conjugation to carriers or other techniques well known in the art. The protein or peptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). Such antibodies are useful as diagnostics for the intact or disrupted gene, and also as research tools for identifying either the intact or disrupted gene.

The invention will be further illustrated by the following non-limiting exemplifications:

EXAMPLES

Azoospermic Males

Figure 5C:
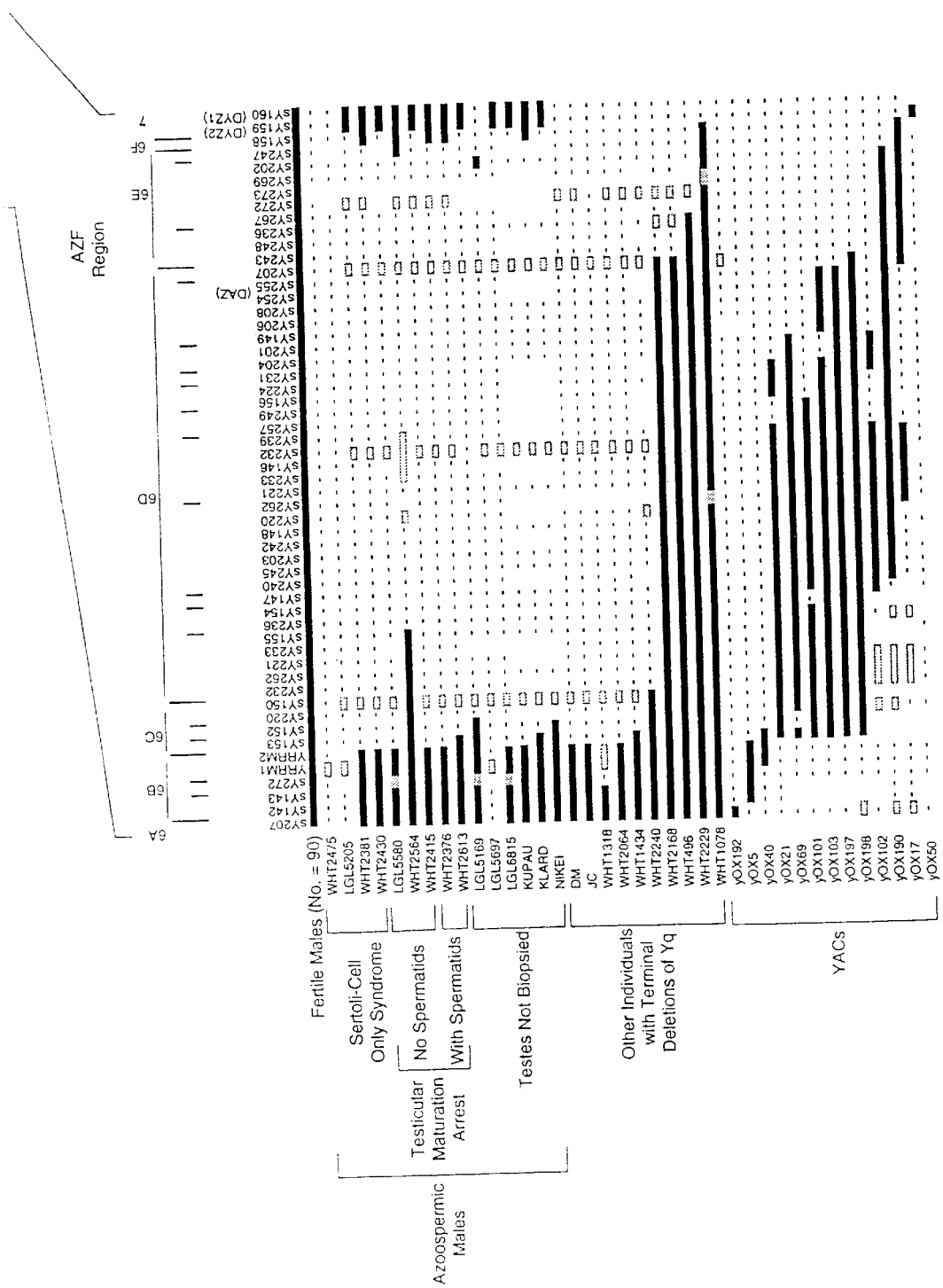
Figure 6C:
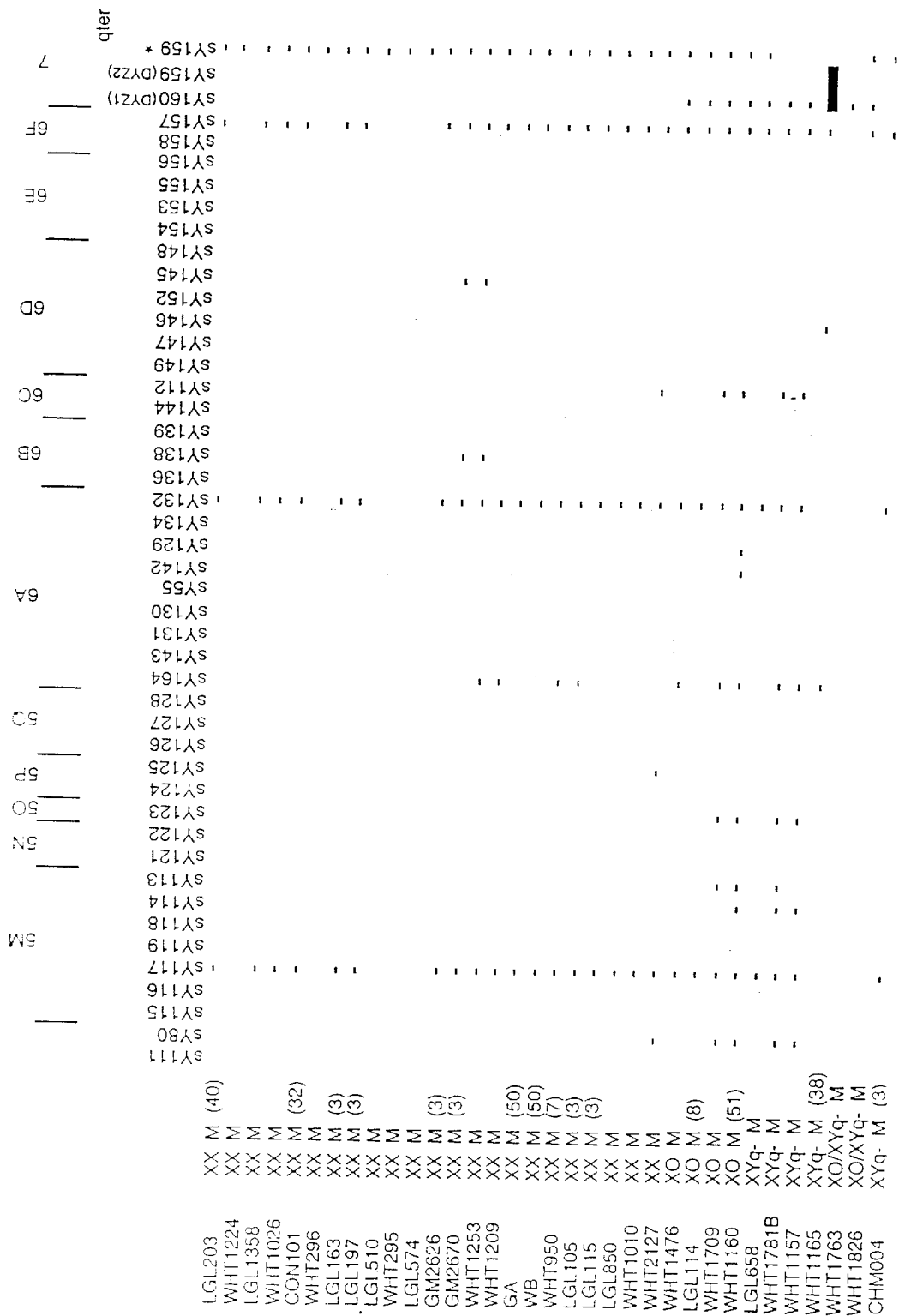
Figure 6G:
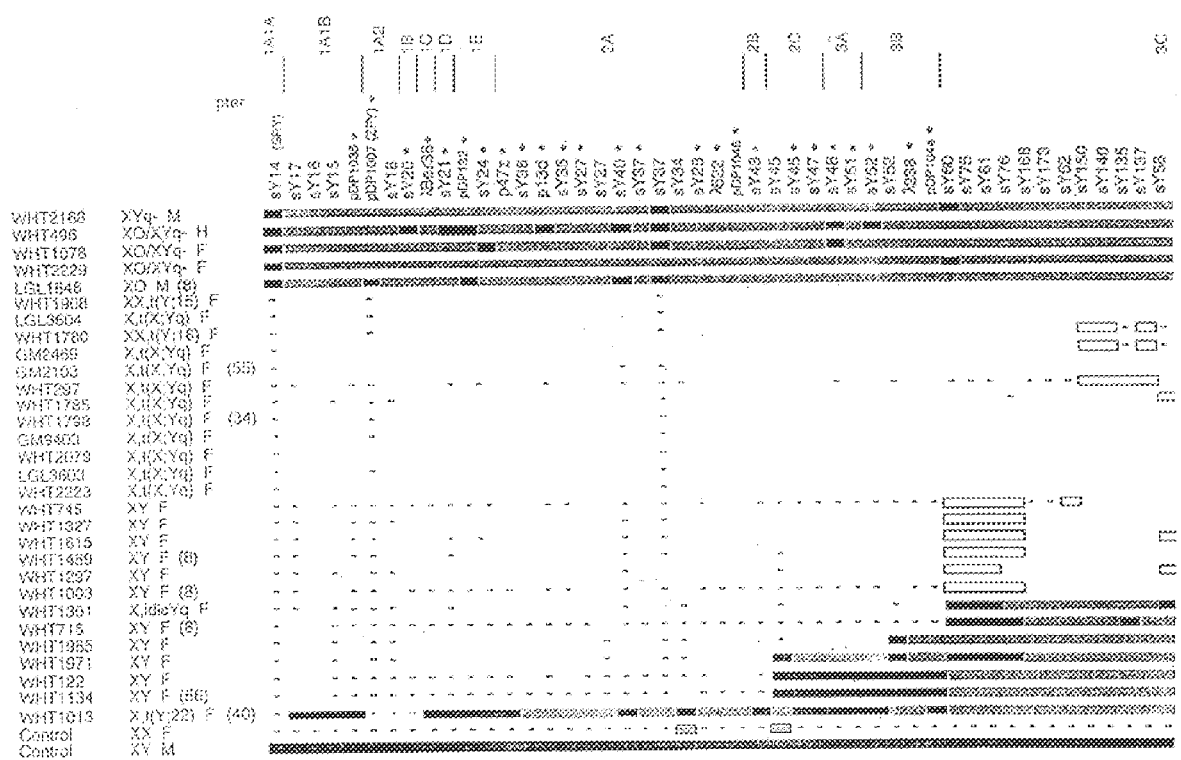
Figure 6B:
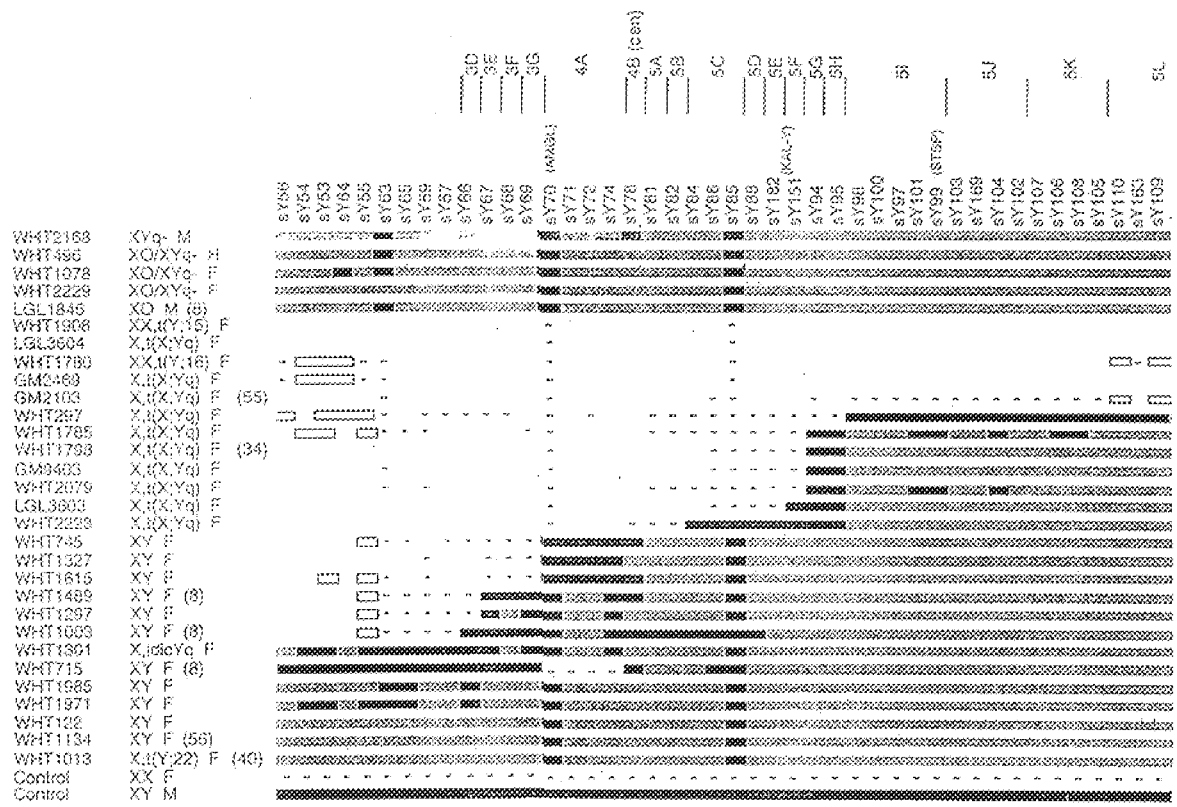
Figure 6I:
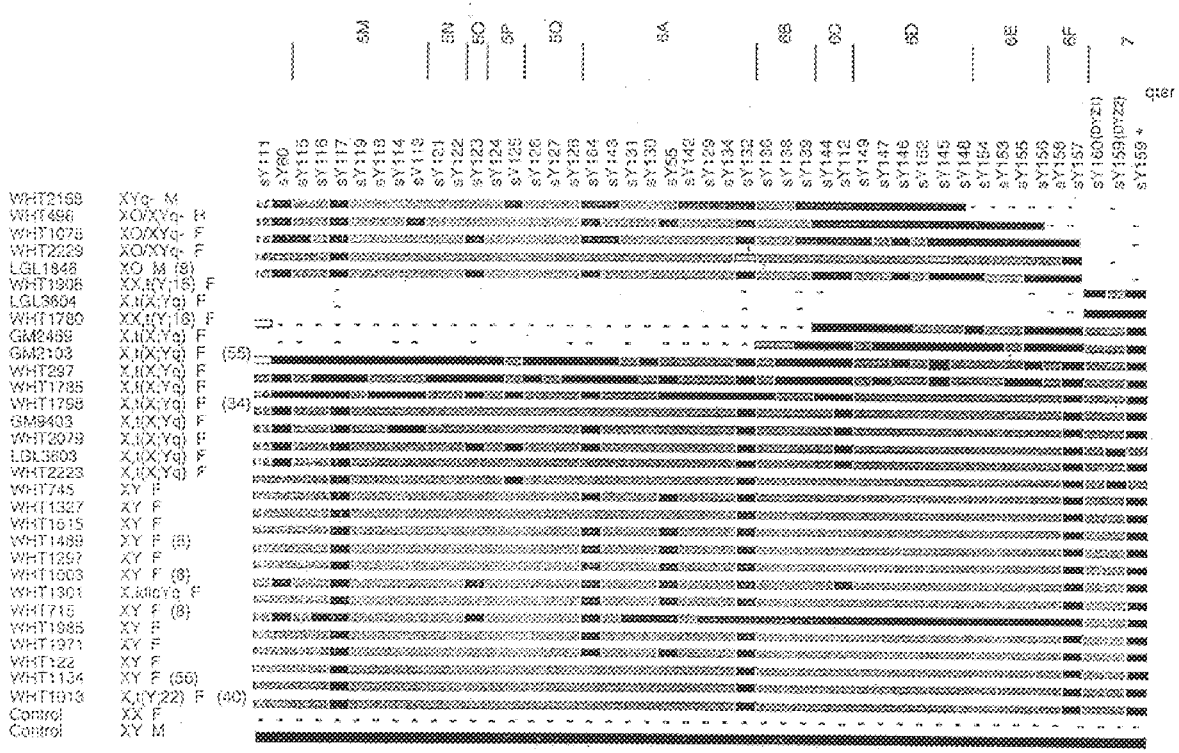

Blood samples were obtained from 71 infertile human males who had testes biopsies. These biopsies showed 32 patients with Sertoli-cell only syndrome, 30 patients with Testicular Maturation Arrest, and 3 patients with both Sertoli-cell only and Testicular Maturation Arrest. Six additional undiagnosed azoospermic males were examined as well. Sequence-tagged sites (STS) from existing Y chromosome maps (Foote, et al., *Science*, 258:60–66, (1992)), were incorporated with new STSs to serve as markers to assay (FIGS. 5A, 5B and 5C). The Y chromosomes of the 71 patients were studied for abnormalities, especially deletions. The presence of each marker was determined by polymerase chain reaction (PCR) amplification and scoring the presence of the product after agarose gel electrophoresis. The PCR conditions consisted of a 5 minute cycle at 94° C., 35 cycles consisting of 1 minute at 94° C., 1.5 minutes at 58° C. and 1 minute at 72° C., and a final 5 minutes at 72° C. Absence of a marker indicated deletion of the region of the chromosome corresponding to that STS. Nine patients were found to have deletions in the Y chromosome. Six of the fathers of these 9 males were screened and no deletions were found, indicating a de novo mutation. The deletions in 8 of the 9 patients were found to be overlapping and within the 6E deletion interval of the Y chromosome (D. Vollrath et al., Science, 258:52–59 (1992)). The one non-overlapping deletion was more proximal on the chromosome, possibly indicative of another gene or region for future study.

Yeast artificial chromosomes (YACs) that spanned the 6E interval were identified. The ends of these YACs were sequenced by ABI automated sequencing to isolate new markers to refine the Y chromosome maps. Additional markers were constructed using subtraction techniques (Rosenberg et al. (1994)). Pooled markers were then used as probes to obtain 5-fold cosmid coverage from the Lawrence Livermore Chromosome Y Cosmid Library LLOYCNO3"M". This produced 124 cosmids, 76% of which contain STSs that fall in the 6E deletion interval. Sixty cosmids were subcloned from yOX17, a 920-kb YAC spanning most of the deletion region. Three P1 clones containing marker sy202 were obtained from Genome Systems to provide fuller coverage of the distal region.

Cosmid #316 (Lawrence Livermore address: Plate 35, row G, column 3), cosmid #325 (Lawrence Livermore address: Plate 48, row D, column 5) and cosmid #330 (Lawrence Livermore address: Plate 59, row H, column 4) were obtained by hybridization. These cosmids were subcloned into exon-trapping vector pSPL3, a vector containing splice donor and acceptor sites. This vector was then transfected into mammalian COS-7 cells according to the exon-trapping system of GibcoBRL/Life Technologies, Cat. No. 18449-017. The exon-trapped exons were then amplified and sequenced using polymerase chain reactions (PCR) and automated sequencing.

The results of the exon-trapping and sequencing indicated that there was one clear cut transcription unit in the interval of interest. The blood DNA of the 8 patients was then probed with a pair of primers from within the gene to confirm that this sequence was indeed missing in males with reduced sperm count. Table 1 list primers used to confirm that this gene is missing in infertile men with reduced sperm counts. Study of tissue from the spleen, thymus, prostate, ovary, small intestine, colon, leukocytes and testis indicate that the DAZ transcript is primarily expressed in the testis.

The sequenced exons produced by the exon-trapping system were then used in a hybridization screen against a Clonetech genomic adult human cDNA λDR2 testes library. One hundred cDNAs were obtained, and two, which contained the same primer bands (#3115–16 and #3125–26) as seen in the original blood sample, were sequenced. The nucleotide sequences of these cDNAs (#66B and 98B) are shown in FIG. 1 SEQ ID NO: 1) and FIG. 2 (SEQ ID NO: 2).

The sequenced exons were also analyzed by GRAIL, FASTN and BLAST to identify potential coding regions and/or homology with known sequences. From this resulting data, it was determined that the DAZ gene is a member of the gene family encoding RNA binding proteins such as poly-A binding protein, hnRNPa1, sex lethal, and a previously identified Y-chromosome gene, YRRM. The nucleotide sequence bears little resemblance to any of these family members, but the RNA binding domains are conserved at the protein level. The closest relative appears to be poly-A binding protein (see Table 2).

TABLE 2

| | RNA Binding Domain | |
|---|---|---|
| | RNP2 | RNP1 |
| RNA BINDING CONSENSUS SEQUENCE: | LFVGNL (SEQ ID NO:9) or IYIKGM (SEQ ID NO:10) | KGYGFVXF (SEQ ID NO:12) |
| POLY-A BINDING PROTEIN: | LFVGNL | KGYGFVNF (SEQ ID NO:13) |
| DAZ: | LFVGGI (SEQ ID NO:11) | KGYGFVSF (SEQ ID NO:14) |

The results of a Northern Blot performed on the exons obtained from exon-trapping showed that the total gene is approximately 3.1 kb. The three cDNAs currently sequenced, #66B, 93B and 98B (pDP #1575, #1576 and #1577), contain a total of 2.5 kb of the sequence. The rest of the sequence was obtained by probing a Clonetech genomic adult human cDNA λDR2 testes library with the ends of the known sequences and using PCR to amplify and sequence the sequence obtained thereby. A RACE protocol (5'-Amplifinder; Clontech) was used to capture the 5' portion of the DAZ transcript. Human adult testis RNA was employed as the starting template and the following two DAZ oligonucleotides were used as gene-specific primers: AAC-GAAACAAATCCATAGCCTTTG (SEQ ID NO: 16) for cDNA synthesis and CTCGCTCGCCCAGAACCGTATC-TACCAAAGCA (SEQ ID NO: 17) for secondary amplification. The resulting PCR product (approximately 500 bp) were cloned (TA cloning system; Invitrogen) and sequenced.

TABLE 1

| OLIGO NO. | SEQUENCE | EXON CLONE# | PAIR WITH | PRODUCT SIZE | Yspec. larger | sY No. |
|---|---|---|---|---|---|---|
| 3115 | GGGTGTTACCAGAAGGCAAA (SEQ ID NO: 3) | ET316-13;-10 | 3116 | 400 | yes | 254 |
| 3116 | GAACCGTATCTACCAAAGCAGC (SEQ ID NO: 4) | ET316-13;10 | 3115 | 400 | | |
| 3123 | GTTACAGGATTCGGCGTGAT (SEQ ID NO: 5) | ET325-17 | 3124 | 125 | yes | 258 |
| 3124 | CTCGTCATGTGCAGCCAC (SEQ ID NO: 6) | ET325-17 | 3123 | 125 | | |
| 3125 | GCTGCAAATCCTGAGACTCC (SEQ ID NO: 7) | 330-13/23 | 3126 | 102 | yes | 259 |
| 3126 | TTTGCCTTCTGGTAACACCC (SEQ ID NO: 8) | 330-13/23 | 3125 | 102 | | |

Methodology

Testing for Y-specific STSs

Many Y chromosomal STSs for which we tested (FIGS. 5A–C) were described previously (4). The remaining STSs are listed in Table 4 and were generated by nucleotide sequencing of 1) ends of YAC inserts, 2) YAC subtraction products, or 3) exon trapping products. YAC-insert ends were captured by inverse PCR (11) following digestion with HaeIII, AluI and TaqI. Oligonucleotide primers were selected so that nearly all PCR assays could be carried out under identical conditions (4). YRRM primers were as described in reference 12 and corrected in reference 13.

Human genomic DNAs were prepared from blood or lymphoblastoid cell lines. PCR was performed in v-bottom, 96-well plates (MJ Research) in 20 µl volumes in 1.5 mM MgCl$_2$, 5 mM NH$_4$Cl, 10 mM tris (pH8.2), 50 mM KCl, 100 µM dNTP's, with 1 unit of Taq DNA polymerase, 100 to 200 ng of human genomic DNA per reaction, and each primer at 1 µM. Thermocycling usually consisted of an initial denaturation of 5 minutes at 94° C.; 35 cycles of 1 minute at 94° C., 1.5 minutes at 58° C., 1 minute at 72° C.; and, finally, 5 minutes at 72° C. As indicated in Table 4, certain primer pairs were annealed at 62° C. Reactions were stored at 4° C. until they were loaded onto 2 to 4% agarose gels for analysis.

TABLE 4

| STS | Left Primer | Right Primer | Product Size (bp) |
|---|---|---|---|
| sY201* | TGTTGTACGTAGAAAAAGGATATTTTACC (SEQ ID NO: 30) | ATATGGTAAACCACTTTTTAAAATTGCCA (SEQ ID NO: 31) | 99 |
| sY202 | ACAGTTTGAAATGAAATTTTAAATGTGTT (SEQ ID NO: 32) | TGACAAAGTGAGACCCTACTACTA (SEQ ID NO: 33) | 121 |
| sY203 | AAGGATATTTTACCTTTGGTAAT (SEQ ID NO: 34) | GTGGAGCAGTGACCTGAAAT (SEQ ID NO: 35) | 157 |
| sY204 | CCTTTGGTAATATTTTGGTTATAT (SEQ ID NO: 36) | ACTTGGATAA GCAGGAAATG GCTG (SEQ ID NO: 37) | 119 |
| sY206 | ACAGAATTTCAGTTGTATTTTATTT (SEQ ID NO: 38) | ACCCTCCAAGATATTAATTCTTTG (SEQ ID NO: 39) | 143 |
| sY207 | AATTAAAGGACCCTTAAATTCATT (SEQ ID NO: 40) | CCTCTGAAAGATTAATATATGGTTCT (SEQ ID NO: 41) | 153 |
| sY208 | GGACATAGTCCTGCTTAAGAAAAGTGG (SEQ ID NO: 42) | ACGTGGTTCAGGAGGTCTACTATTCTA (SEQ ID NO: 43) | 140 |
| sY220 | ATGGGTGAGAAGCCTGATTGT (SEQ ID NO: 44) | TGGGAAAGCCTGAACTGCC (SEQ ID NO: 45) | 109 |
| sY221 | GTAAGCCCCAGATACCCTCC (SEQ ID NO: 46) | AAATTGTTTGGAAAAGGACACC (SEQ ID NO: 47) | 113 |
| sY224 | ATAGTTAGTTTTGTGGTAACAT (SEQ ID NO: 48) | CATAGCCTCTATGCAGATGGG (SEQ ID NO: 49) | 158 |
| sY231 | ATTGATGTGTTGCCCCAAT (SEQ ID NO: 50) | AGAGTGAACTTTAAATCCCAGCC (SEQ ID NO: 51) | 149 |
| sY232 | GACTCTACCACTTGGGCTCAATTT (SEQ ID NO: 52) | AGATGTACCCAAGGCCACTG (SEQ ID NO: 53) | 91 |
| sY233 | AGTTAGTAAGCCCCAGTTATCCTCC (SEQ ID NO: 54) | TTTGGAAAAGGACACCTTATTAGCCA (SEQ ID NO: 55) | 115 |
| sY236 | CCCCATCGGTAAACCAAATCA (SEQ ID NO: 56) | CCCATTGAAGTTTCAAGGTGTCA (SEQ ID NO: 57) | 94 |
| sY230 | CATTCATCTTCCCTTTTGAAGG (SEQ ID NO: 58) | ATGCAAGTCGCAGGAAATCT (SEQ ID NO: 59) | 200 |
| sY240 | TCAAATAGCAGCAATTTAATAT (SEQ ID NO: 60) | GCACCTGAAGAGCTGCTTG (SEQ ID NO: 61) | 247 |
| sY242 | ACACAGTACCAGCGGGAGTT (SEQ ID NO 62) | TCTGCCACTAAACRTGTAAGCTCC (SEQ ID NO: 63) | 233 |
| sY243 | GTTTCTTCATAAGCAACCAAATTG (SEQ ID NO: 64) | CAGATTATGCCACTGCCCTT (SEQ ID NO: 65) | 118 |
| sY245 | TTACTTCCTTAAGTCAAAGCGG (SEQ ID NO: 66) | CTGAGACAGCAAGACCAATCC (SEQ ID NO: 67) | 103 |
| sY247 | CTGGACAAAGCCTTGGAAAA (SEQ ID NO: 68) | CTGCATGTCAATTGTGGGAC (SEQ ID NO: 69) | 114 |
| sY248 | CATTGGCATGAATGTGTATTC (SEQ ID NO: 70) | CTCTGGGACAAGTGTTCCTT (SEQ ID NO: 71) | 94 |
| sY249 | GACAAAGGGCTGATGATTTA (SEQ ID NO: 72) | CATCACCTTTACTTTTTAAATGG (SEQ ID NO: 73) | 114 |
| sY254* | GGGTGTTACCAGAAGGCAAA (SEQ ID NO: 74) | GAACCGTATCTACCAAAGCAGC (SEQ ID NO: 75) | 107 |
| sY255* | GTTACAGGATTCGGCGTGAT (SEQ ID NO: 76) | CTCGTCATGTGCAGCCAC (SEQ ID NO: 77) | 126 |
| sY257 | AGGTTGTTTGGCCTTGAGC (SEQ ID NO: 78) | TCTATGATCTGTACCCGGTGC (SEQ ID NO: 79) | 123 |
| sY262 | AGCTCACTGCAAGCAACAGA (SEQ ID NO: 80) | CCACCATCCCCCTTCTTC (SEQ ID NO: 81) | 100 |
| sY267 | GAATGTGTATTCAAGGACTTCTCG (SEQ ID NO: 82) | TACTTCCTTCGGGGCCTCT (SEQ ID NO: 83) | 102 |
| sY269 | CTCTGGGACAAGTGTTCCTTG (SEQ ID NO: 84) | CATTGGCATGAATGTGTATTCA (SEQ ID NO: 85) | 94 |
| sY272 | GGTGAGTCAAATTAGTCAATGTCC (SEQ ID NO: 86) | CCTTACCACAGGACAGAGGG (SEQ ID NO: 87) | 93 |
| sY273 | GGTCTTTAAAAGGTAGAGTCAAATT (SEQ ID NO: 88) | AGACAGAGGGAACTTCAAGACC (SEQ ID NO: 89) | 95 |

*within the DAZ gene

We also tested individual Y-derived YACS (5) for STSs, in which case we employed 5 to 10 ng of total yeast genomic DNA as template and an annealing temperature of 62° C.

YAC subtraction

The subtraction protocol of Rosenberg et al. (14) was modified for use with YAC DNAs. DNAs from 66 overlapping YACs spanning most of the Y chromosome's euchromatic region (5) were separated from yeast chromosomes by pulsed-field electrophoreses on 1.2% low-melt agarose gels, excised and purified using Geneclean (Bio 101). "Tracer" was prepared using DNA pooled from eight overlapping YACs (yOX69, yOX101, yOX102, yOX103, yOX104, yOX190, yOX192, yOX198) blanketing the AZF region. 100 ng of this DNA was digested with SAu3A and ligated to Sau3A-compatible PCT adapter (an equimolar mixture of GACACTCTCGAGACATCACCGTCC (SEQ ID NO: 90) and phosphorylated GATCGGACGGTGATGTCTC-GAGAGTG (SEQ ID NO: 91)). "Drivers" were prepared from total yeast genomic DNA (strain AB1380) and form DNA pooled from 58 YACs spanning the remainder of the euchromatic portion of the Y chromosome. Yeast genomic DNA (1 µg) or pooled YAC DNA (100 ng) was sonicated to an average length of 1 kb, treated with Klenow fragment of DNA polymerase to produce blunt ends, and ligated to blunt-end PCR adapter (an equimolar mixtures of AATTCT-TGCGCCTTAAACCAAC (SEQ ID NO: 94) and phosphorylated GTTGGTTTAAGGCGCAAG (SEQ ID NO: 95)). Tracer and driver DNAs were then amplified separately using oligonucleotides Ol25 and OL31DB, respectively, as PCR primers (14). Subtractive hybridizations were carried out as previously described after combining the following in a total volume of 4 µl: 4 ng of amplified tracer DNA; 7 µg of amplified, biotinylated YAC driver DNA; 3 µg of amplified, biotinylated yeast genomic driver DNA; 20 µg of yeast tRNA; 5 µg of oligonucleotide OL30; and 2 µg of oligonucleotide OL25. Individual products of subtraction were sequenced after digesting bulk product with Sau3A and cloning into the BamHI site of plasmid pBluescript KS(+) (Stratagene). To increase the sequence complexity of the subtraction product, an additional round of subtractive hybridization was performed using, as a third driver, 2 µg of DNA from 130 subtraction clones that had been pooled, amplified, and biotinylated as described above. The resulting subtraction product, in bulk, was radiolabeled and hybridized to high-density arrays of an 11,700-clone, Y-enriched cosmid library (LLOYNC03; Human Genome Center, Lawrence Livermore National Laboratory, Livermore, Calif.) according to the procedure of Holland et al. (15), resulting in identification of 120 cosmid clones.

Exon trapping

Substrates for exon trapping (16) included 120 cosmids identified by hybridization to YAC subtraction product, 60 cosmids constructed by subcloning YAC yOX17 in Super-Cos1 (Stratagene), and three P1 clones identified by commercial screening (Genome Systems). These genomic clones were digested with BamHI and BglII, individually subcloned into pSPL3 (Gibco-BRL) and transfected into COS7 cells. After 48 hours growth, RNA was harvested using Trizol (Gibco-BRL). cDNA was synthesized, and clones that contained potential intron-exon boundaries were identified by PCR using primers flanking the cloning sites. These exon trapping products were sequenced, and from these sequences STSs were developed.

Characterization of potential exons

We further characterized exon trapping products whose corresponding STSs were male-specific and mapped to the AZF region, including exon 325.7 (subcloned as plasmid pDP1593), which proved to derive from the DAZ gene. To confirm male specificity and to look for evidence of transcription, potential exons were labeled with $^{32}$P-dCTP by random priming and hybridized to Southern and Northern blots as previously described (17). Putative exons were then used as hybridization probes in screening a cDNA library (HL1161X, Clontech) constructed by oligo (dT) priming of mRNA from the testes of four human adults; hybridization (at 47° C.) and washing conditions were as published (17). Nucleotide sequencing of DAZ cDNA clones was performed as previously described (17). Since the composite length of DAZ cDNA clones was considerably shorter than the 3.5-kb transcript observed on Northern blots, we used a RACE protocol (5'-Amplifinder; Clontech) to capture the 5' portion of the DAZ transcript. We employed human adult testis RNA as starting template and the following two DAZ oligonucleotides as gene-specific primers: AACGAAACAAATCCAT-AGCCTTTG (SEQ ID NO: 92) (for cDNA synthesis) and CTCGCTCGCCCAGAACCGTATCTACCAAAGCA (SEQ ID NO: 93) (for secondary amplification). The resulting PCR products (approximately 500 bp) were cloned (TA cloning system; Invitrogen) and sequenced.

Oligospermic Males

Idiopathic oligospermia, defined as the presence of less than 20 million sperm per ml of semen, is the most common cause of male infertility. About three to four percent of men have severe defects in sperm production resulting in oligospermia, a principal or contributing factor in perhaps one fifth of infertile couples. Progress toward medical therapies to correct oligospermia has been slow, at least in part, because the etiology of the disorder is not understood. In particular, little is known about the possible contributions of genetic factors.

The wide range of testicular histologies observed in azoospermic men with AZF deletions led us to entertain the possibility that less severe spermatogenic defects could also be caused by AZF's absence. What if the Azoospermia Factor is not absolutely required for completion of spermatogenesis? Though the AZF gene or gene family was originally defined and more recently mapped in the context of azoospermia, we wondered whether the gene's absence might sometimes result in oligospermia. Indeed, in a few cases, Y chromosomal variants have been reported in oligospermic men (1), but in no case prior to our current study was the variant shown to be a de novo mutation, and thus no causal link could be established. In searching for such definitive evidence of causality, we chose to further focus our studies on men with severe oligospermia.

Methods

Screening for Y Chromosomal Deletions

We screened severely oligospermic men for Y chromosome deletions using DNA probes. Cytologically, the Y chromosome consists of a euchromatic region and a heterochromatic region. As the heterochromatin appears to be dispensable with regard to fertility (2,3), we concentrated on the euchromatin, for which a comprehensive map of ordered DNA landmarks and overlapping recombinant DNA clones has been assembled (4,5). Genomic DNAs were prepared from peripheral blood samples (6) from 35 men with total motile sperm counts (per ejaculate) of 40,000 to 1 million. Using the polymerase chain reaction (PCR), we tested each oligospermic man for the presence of 118 Y-DNA landmarks (more precisely, STSs, or sequence-tagged sites previously shown to blanket the euchromatic region of the Y chromosome. We took two precautions to minimize false negative results. First, we only used PCR assays that reliably gave positive results when tested on 90 fertile men. Second, we did not record an STS as absent from a patient unless at least three successive attempts at PCR amplification yielded negative results.

Sperm DNA

In the case of patient WHT2712, spermatozoa were purified from ejaculate by centrifugation on a MiniPercoll gradient (7). To prepare DNA, 50,000 sperm were incubated for 1 hr at 37° C. in 20 μl of a solution containing 0.05 mg/ml proteinase K, 50 mM KCl, 10 mM Tris pH 8.3, 1.5 mM MgCl$_2$, 20 mM dithiothreitol, and 1.7 μM sodium dodecyl sulfate. Proteinase K was then inactivated by heating the samples to 85° C. for 5 minutes, and 100 μl of PCR mix (containing 1.5 mM MgCl$_2$, 5 mM NH$_4$Cl, 10 mM Tris (pH 8.2), 50 mM KCl, and 100 μM dNTP's) was added to each sample (8). This sperm DNA was tested for a subset of the Y-chromosomal landmarks, again by PCR.

Y-chromosomal STSs

Most of the Y-chromosome STSs for which we tested (FIGS. 5A–5C), as well as the PCR and electrophoresis conditions employed, were described previously (4,9). Six new STSs were developed for this study, and their designations and oligonucleotide primer sequences are shown in Table 3.

If the Yq deletions actually caused the severe oligospermia in WHT2615 and WHT2712, then one would expect the deletions to represent new mutations not present in their fathers. Both fathers were found to carry intact Y chromosomes. We concluded that the deletions of the AZF region are the cause of oligospermia in these two cases.

AZF-Deleted, Y-Bearing Sperm

The Y-DNA tests described in the previous section were all performed on blood, a conventional and readily accessible source of DNA for genetic testing. However, our finding of AZF-region deletions in leukocytes from oligospermic men raised important questions about the DNA in their sperm. If AZF if absolutely required for completion of spermatogenesis, then one might suppose that the sperm produced by the two oligospermic men under study could carry either an X or an intact Y chromosome, but never an AZF-deleted Y chromosome. This would be possible if the two oligospermic men under study are testicular mosaics for a cell line with an intact Y chromosome, in which case the de novo AZF deletions reported would have arisen as somatic mutations, after fertilization, rather than in the fathers' germlines. On the other hand, if these oligospermic men produce some sperm carrying AZF deleted Y

TABLE 3

| STS | Gene | Left Primer | Right Primer | Product Size (bp) |
|---|---|---|---|---|
| sY277 | DAZ | GGGTTTTGCCTGCATACGTAATTA (SEQ ID NO: 18) | CCTAAAAGCAATTCTAAACCTCCAG (SEQ ID NO: 19) | 275 |
| SsY279 | DAZ | CCACCTCATGGTAGTAAAATTGTA (SEQ ID NO: 20) | CTCTTATTTATCTTATTGCTACAACG (SEQ ID NO: 21) | 150 |
| sY283 | DAZ | CAGTGATACACTCGGACTTGTGTA (SEQ ID NO: 22) | GTTATTTGAAAAGCTACACGGG (SEQ ID NO: 23) | 375 |
| sY274 | RPS4Y | TTAAGGGGACAGTATTTCAACTTC (SEQ ID NO: 24) | CCACATTTAAACTGAGTACAGTCC (SEQ ID NO: 25) | 350 |
| sY238 | ZFY | AACAAGTGAGTTCCACAGGG (SEQ ID NO: 26) | GCAAAGCAGCATTCAAAACA (SEQ ID NO: 27) | 350 |
| sY276 | AMELY | CCTACCGCATCGTGAATTTC (SEQ ID NO: 28) | TCTGTATGTGGAGTACACATGG (SEQ ID NO: 29) | 200 |

Results
De Novo AZF Deletions in Two Oligospermic Men

We detected Y chromosome deletions in two men, both of when were severely oligospermic and had poor sperm motility and morphology. In the first patient, WHT2615, repeated semen analyses yielded sperm counts of 50,000 to 100,000 per ml, with 20 to 30% of sperm motile and 10% of sperm with normal morphology. In the second patient, WHT2712, repeated semen analyses yielded sperm counts of 40,000 to 90,000 per ml, with 30 to 40% of sperm motile and 10 to 25% of sperm with normal morphology. Apart from infertility, these two unrelated individuals were in good health.

In both WHT2615 and WHT2712, we discovered deletions of small, interstitial portions of Yq, the long arm of the Y chromosome. In both men we detected the presence of the bulk of the Y chromosome, including the sex-determining gene SRY as well as RPS4Y, ZFY, YRRM, TSPY, AMELY, the centromere, and the heterochromatic region. However, in WHT2615 and WHT2712, we detected the absence of 43 and 44, respectively, of the 118 Y-chromosomal STSs (sequence-tagged sites) tested. The absent STSs are all clustered in the AZF region, the portion of Yq commonly deleted in azoospermic men, and they include the DAZ gene. The Yq deletions observed in the two oligospermic men overlap substantially not only with each other but also with the deletions we previously observed in azoospermic men.

chromosomes, issues of genetic counseling would arise, since efforts to father children via intracytoplasmic sperm injection or other in vitro fertilization techniques might propagate the Y-chromosomal defect and the infertility for which it is responsible.

To test these possibilities, we carried out DNA studies on the rare sperm produced by one of the two AZF-deleted oligospermic men, WHT2712. We tested sperm DNA prepared from an unrelated, fertile control man and from WHT2712 for a subset of Y-chromosomal STS located within and just outside the region deleted in WHT2712's leukocytes. As expected, the fertile man's sperm carried an intact Y chromosome. Oligospermic male WHT2712 was also found to produce Y-bearing sperm, but these carry a deletion of the AZF region—the same deletion that was found in his blood.

Thus, we found that severe oligospermia is caused, in some cases, by newly arising deletions on the Y chromosome. These deletions are of interstitial, submicroscopic portions of the Y chromosome's long arm (Yq); they encompass the entirety of the previously defined Azoospermia Factor (AZF) region and include the DAZ gene; and they are not present in the fathers of the oligospermic men. This last observation is crucial in that it establishes that these deletions were not inconsequential polymorphisms (10) but were in fact the cause of oligospermia. The Yq deletions we observed in two oligospermic men are remarkably similar in location and extent to those we had reported in azoospermic men with Sertoli-cell-only syndrome or complete testicular maturation arrest, indicating that these disorders are not etiologically distinct (when associated with Yq deletions) but represent clinically diverse manifestations of the same underlying genetic cause.

Equivalents

Those skilled in the art will recognize or be able to ascertain, using no more than routine experimentation, many equivalents to the specific embodiments of the invention described specifically herein. Such equivalents are intended to be encompassed in the scope of the following claims.

REFERENCES

1. Kobayashi K., Mizuno K., Hida A., et al. PCR analysis of the Y chromosome long arm in azoospermic patients: evidence for a second locus required for spermatogenesis. *Hum Mol Genet* 1994; 3: 1965–67.
2. Andersson M., Page D. C., Pettay D., et al. Y;autosome translocations and mosaicism in the aetiology of 45,X maleness: assignment of fertility factor to distal Yq11. *Hum Genet* 1988; 79: 2–7.
3. Borgaonkar D. S., Hollander D. H. Quinacrine fluorescence of the human Y chromosome. *Nature* 1971; 230: 52.
4. Vollrath D., Foote S., Hilton A., et al. The human Y chromosome: a 43-interval map based on naturally occurring deletions. *Science* 1992; 258: 52–59.
5. Foote S., Vollrath D., Hilton A., Page D. C. The human Y chromosome: overlapping DNA clones spanning the euchromatic region. *Science* 1992; 258: 60–66.
6. Page D. C., Mosher R., Simpson E. M., et al. The sex-determining region of the human Y chromosome encodes a finger protein. *Cell* 1987; 51: 1091–104.
7. Ord T., Patrizio P., Marello E., Balmaceda J. P., Asch R. H. MiniPercoll: a new method of semen preparation for IVF in severe male factor infertility. *Hum Reprod* 1990; 5: 987–89.
8. Gyllensten U. Haplotype analysis from single sperm or diploid cells. In: Innis M. A., Gelfand D. H., Sninsky J. J., White T. J., eds. PCR Protocols. Vol. 1. San Diego, Calif.: Academic Press, 1990: 300–06.
9. Reijo R., Lee T. Y., Salo P., et al. Diverse spermatogenic defects in humans caused by Y chromosome deletions encompassing a novel RNA-binding protein gene. *Nature Genet* 1995; 10: 383–93.
10. Nakahori Y., Kobayashi K., Komaki R., Matsushita I., Nakagome Y. A locus of the candidate gene family for azoospermia factor (YRRM2) is polymorphic with a null allele in Japanese males. *Hum Molec Genet* 1994; 3: 1709.
11. Haldi, M. et al. Large human YACs constructed in a rad52 strain show a reduced rate of chimerism. *Genomics* 24, 478–484 (1995).
12. Ma, K. et al. A Y chromosome gene family with RNA-binding protein homology: Candidates for the azoospermia factor AZF controlling human spermatogenesis. *Cell* 75, 1287–1295 (1993).

REFERENCES CONTINUED

13. Kobayashi, K. et al. PCR analysis of the Y chromosome long arm in azoospermic patients: evidence for a second locus required for spermatogenesis. *Hum. Mol. Genet.* 3, 1965–1967 (1994).
14. Rosenberg, M., Przybylska, M. & Straus, D. RFLP subtraction: A method for making libraries of polymorphic markers. *Proc. Natl. Acad. Sci. (USA)* 91, 6113–6117 (1994).
15. Holland, J., Coffey, A. J., Giannelli, F. & Bentley, D. R. Vertical integration of cosmid and YAC resources for interval mapping on the X-chromosome. *Genomics* 15, 297–304 (1993).
16. Duyk, G. M., Kim, S., Meyers, R. M. & Cox, D. R. Exon trapping: A genetic screen to identify candidate transcribed sequences in cloned mammalian genomic DNA. *Proc. natn. Acad. Sci. (USA)* 87, 8995–8999 (1990).
17. Fisher, E. M. C. et al. Homologous ribosomal protein genes on the human X and Y chromosomes: Escape from X inactivation and possible implications for Turner syndrome. *Cell* 63, 1205–1218 (1990).

The invention claimed is:

1. An isolated cDNA of a gene present in interval 6D and/or 6E of the distal portion of the long arm of the human Y chromosome, which is a member of the DAZ gene family.

2. An isolated cDNA according to claim 1, comprising SEQ ID NO: 15.

3. An isolated gene which is a member of the DAZ gene family and which specifically hybridizes to a DNA sequence selected from the group consisting of:
   a) SEQ ID NO: 4;
   b) the complement of SEQ ID NO: 4;
   c) SEQ ID NO: 5;
   d) the complement of SEQ ID NO: 5;
   e) SEQ ID NO: 6;
   f) the complement of SEQ ID NO: 6;
   g) SEQ ID NO: 7;
   h) the complement of SEQ ID NO: 7;
   i) SEQ ID NO: 8;
   j) the complement of SEQ ID NO: 8;
   k) SEQ ID NO: 9;
   l) the complement of SEQ ID NO: 9;
   m) SEQ ID NO: 15; and
   n) the complement of SEQ ID NO: 15.

4. An isolated cDNA of a gene present in interval 6D and/or 6E of the distal portion of the long arm of the human Y chromosome, whose alteration is associated with reduced sperm count, which is a member of the DAZ gene family and which comprises the DNA sequence of SEQ ID NO: 1.

5. An isolated cDNA according to claim 4 which further comprises SEQ ID NO: 2.

6. An isolated cDNA according to claim 5, which encodes a protein which is an RNA binding protein.

7. A protein encoded by an isolated cDNA of a gene present in interval 6D and/or 6E of the distal portion of the long arm of the human Y chromosome, whose alteration is associated with reduced sperm count and which comprises SEQ ID NO: 15.

8. An isolated nucleotide sequence selected from the group consisting of:
   a) SEQ ID NO: 4;
   b) the complement of SEQ ID NO: 4;
   c) SEQ ID NO: 5;

d) the complement of SEQ ID NO: 5;
e) SEQ ID NO: 6;
f) the complement of SEQ ID NO: 6;
g) SEQ ID NO: 7;
h) the complement of SEQ ID NO: 7;
i) SEQ ID NO: 8;
j) the complement of SEQ ID NO: 8;
k) SEQ ID NO: 9;
l) the complement of SEQ ID NO: 9;
m) SEQ ID NO: 15; and
n) the complement of SEQ ID NO: 15.

9. An isolated nucleotide sequence comprising the nucleotide sequence of SEQ ID NO: 1, or the complement of said nucleotide sequence.

10. An isolated nucleotide sequence comprising the nucleotide sequence of SEQ ID NO: 2, or the complement of said nucleotide sequence.

* * * * *

SEQUENCE LISTING ( 1 ) GENERAL INFORMATION:

( i i i ) NUMBER OF SEQUENCES: 96

( 2 ) INFORMATION FOR SEQ ID NO:1:

( i ) SEQUENCE CHARACTERISTICS:
        ( A ) LENGTH: 702 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
TCAGCTGGGG   TCTACTCCGA   GGGTTCGCCC   GACCTTGGTT   TTCCTTACAC   CTTAGCCTTT         60

GGCTCCTTGA   CCACTCGAGC   CCCACAGGTG   TTCCAGCGGA   CTTCACCAGC   AGACCCAGAA        120

GTGGTGGGTG   AAACACTGCC   TCTGTTCCTC   CTTGAGCCTG   TCGGGAGCTG   CTGCCTGCCA        180

CCACCATGTC   TGCTGCAAAT   CCTGAGACTC   CAAACTCAAC   CATCTCCAGA   GAGGCCAGCA        240

CCCAGTCTTC   ATCAGCTGCA   GCTAGCCAAG   GCTGGGTGTT   ACCAGAAGGC   AAAATCGTGC        300

CAAACACTGT   TTTTGTTGG    TGGAATTGAT   GCTAGGATGG   ATGAAACTGA   GATTGGAAGC        360
```

| | | | | | |
|---|---|---|---|---|---|
| TGCTTTGGTA | GATACGGTTC | AGTGAAAAGA | AGTGAAGATA | ATCACGAATC | GAACTGGTGT | 420
| TCCAAAGGCT | ATGGATTTGT | TTCGTTTGTT | AATGACGTGG | ATGTCCAGAA | GATTAGTAGG | 480
| ATCACAGAAT | ACATCTCCAT | GGGTAAAAAG | CTGAAGCTGG | GCCCTGCAAT | CAGGAAACAA | 540
| AAGTTATGTG | CTCGTCATGT | GCAGCCACGT | CCTTTGGTAG | TTAATCCTCC | TCCTCCACCA | 600
| CAGTTTCAGA | ACGTCTGGCG | GAATCCAAAC | ACTGAAACCT | ACCTGCAGCC | CCAAATCACG | 660
| CCGAATCCTG | TAACTCAGTA | CGTTCAGTCT | GCTGCAAATC | CT | | 702

(2) INFORMATION FOR SEQ ID NO:2:

(i) SEQUENCE CHARACTERISTICS:
        (A) LENGTH: 428 base pairs
        (B) TYPE: nucleic acid
        (C) STRANDEDNESS: double
        (D) TOPOLOGY: linear (xi) SEQUENCE DESCRIPTION: SEQ ID NO:2:

| | | | | | |
|---|---|---|---|---|---|
| GAGTAATCAN | ATGCANGTCA | TACTGAATTT | GTACTGTATC | ACAGGTACTT | CTTGGAGAAG | 60
| TGAAATGCTT | GTGTTCAGAC | TATCAAAATT | GTTAGCTTAC | AAATCAGGTT | TTAAAAACTT | 120
| TTGGAAAGTC | AGTATGTGCT | TTTAAACACT | TAAATGCANG | TCTCANTTTT | TTTTTTTTC | 180
| CGNAGATATC | TTAACATTCT | TCAGTCTCGA | TTATGTGTTA | CTTTAAACTA | TATATTAAAC | 240
| ACAGACCCAG | GTTCTAAATA | AACATCTAAT | GAAGAACAGC | ATCGTTAAGA | TAAAAACTAG | 300
| AGAGTCTAAT | AATACAAGTT | ATACAGAAAG | TTTCAGTGTG | ATTTCCAAAT | TCAGAATTTC | 360
| AGTAATAGTG | GAAAAACTTT | TAGCTTATAT | CACCCAGCAC | TCCCCATGAA | ACTAGATGCT | 420
| GAGAGGCC | | | | | | 428

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:3:

GGGTGTTACC AGAAGGCAAA           20

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:4:

GAACCGTATC TACCAAAGCA GC         22

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:5:

GTTACAGGAT TCGGCGTGAT           20

(2) INFORMATION FOR SEQ ID NO:6:

( i ) SEQUENCE CHARACTERISTICS:
   ( A ) LENGTH: 18 base pairs
   ( B ) TYPE: nucleic acid
   ( C ) STRANDEDNESS: double
   ( D ) TOPOLOGY: linear ( x i ) SEQUENCE DESCRIPTION: SEQ ID NO:6:

CTCGTCATGT GCAGCCAC 18

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:7:

GCTGCAAATC CTGAGACTCC 20

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:8:

TTTGCCTTCT GGTAACACCC 20

( 2 ) INFORMATION FOR SEQ ID NO:9:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:9:

Leu  Phe  Val  Gly  Asn  Leu
1                    5

( 2 ) INFORMATION FOR SEQ ID NO:10:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:10:

Ile  Tyr  Ile  Lys  Gly  Met
1                    5

( 2 ) INFORMATION FOR SEQ ID NO:11:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide (x i) SEQUENCE DESCRIPTION: SEQ ID NO:11:

Leu Phe Val Gly Gly Ile
1               5

(2) INFORMATION FOR SEQ ID NO:12:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:12:

Lys Gly Tyr Gly Phe Val Xaa Phe
1               5

(2) INFORMATION FOR SEQ ID NO:13:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:13:

Lys Gly Tyr Gly Phe Val Asn Phe
1               5

(2) INFORMATION FOR SEQ ID NO:14:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:14:

Lys Gly Tyr Gly Phe Val Ser Phe
1               5

(2) INFORMATION FOR SEQ ID NO:15:

(i) SEQUENCE CHARACTERISTICS:
    (A) LENGTH: 1849 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:15:

| | | | | | |
|---|---|---|---|---|---|
| AGTCGGCCTG | CGCTCCTCAG | CCTGGCGGTT | CTACCTCCGA | GGGTTCGCCC | GCCCTTGGTT | 60 |
| TTCCTTACAC | CTTAGCCTTT | GGCTCCTTTG | ACCACTCGAA | GCCCCACAGC | GTGTTCCAGC | 120 |
| GGACTTCACC | AGCAGACCCA | GAAGTGGTGG | GTGAAACACT | GCCTCTGTTC | CTCCTTGAGC | 180 |
| CTGTCGGGAG | CTGCTGCCTG | CCACCACCAT | GTCTGCTGCA | AATCCTGAGA | CTCCAAACTC | 240 |
| AACCATCTCC | AGAGAGGCCA | GCACCCAGTC | TTCATCAGCT | GCAGCTAGCC | AAGGCTGGGT | 300 |
| GTTACCAGAA | GGCAAAATCG | TGCCAAACAC | TGTTTTTGTT | GGTGGAATTG | ATGCTAGGAT | 360 |
| GGATGAAACT | GAGATTGGAA | GCTGCTTTGG | TAGATACGGT | TCAGTGAAAG | AAGTGAAGAT | 420 |

| | | | | | | |
|---|---|---|---|---|---|---|
| AATCACGAAT | CGAACTGGTG | TGTCCAAAGG | CTATGGATTT | GTTTCGTTTG | TTAATGACGT | 480 |
| GGATGTCCAG | AAGATAGTAG | GATCACAGAT | ACATTTCCAT | GGTAAAAGAG | ACTGATAAAT | 540 |
| TCCGTTGTTA | CTCAAGATGA | CTGCTTCAAG | GGTAAAAGAG | TGCATCGCTT | TAGAAGAAGT | 600 |
| TTGGCAGTAT | TTAAATCTGT | TGGATCCTCT | CAGCTATCTA | GTTTCATGGG | AAGTTGCTGG | 660 |
| TTTTGAATAT | TAAGCTAAAA | GTTTTCCACT | ATTACAGAAA | TTCTGAATTT | TGGTAAATCA | 720 |
| CACTGAAACT | TTCTGTATAA | CTTGTATTAT | TAGACTCTCT | AGTTTATCT | TAACACTGAA | 780 |
| ACTGTTCTTC | ATTAGATGTT | TATTTAGAAC | CTGGTTCTGT | GTTAATATA | TAGTTTAAAG | 840 |
| TAACAAATAA | TCGAGACTGA | AAGAATGTTA | AGATTTATCT | GCAAGGATTT | TTAAAAAATT | 900 |
| GAAACTTGCA | TTTTAAAGTG | TTTAAAAGCA | AATTACTGAC | TTTCAAAAAA | GTTTTAAAA | 960 |
| CCTGATTTGA | AAGCTAACAA | TTTTGGATAG | TCTGAACACA | AGCATTTCAC | TTCTCCAAGA | 1020 |
| AGTACCTGTG | AACAGTACAA | TATTTCAGTA | TTGAGCTTTG | CATTTATGAT | TTATCAAGCT | 1080 |
| GAAGCTGGGC | CCTGCAATCA | GGAAACAAAA | GTTATGTGCT | CGTCATGTGC | AGCCACGTCC | 1140 |
| TTTGGTAGTT | AATCCTCCTC | CTCCACCACA | GTTTCAGAAC | GTCTGGCGGA | ATCCAAACAC | 1200 |
| TGAAACCTAC | CTGCAGCCCC | AAATCACGCC | GAATCCTGTA | ACTCAGCACG | TTCAGGCTTA | 1260 |
| TTCTGCTTAT | CCACATTCAC | CAGGTCAGGT | CATCACTGGA | TGTCAGTTGC | TTGTATATAA | 1320 |
| TTATCAGGAA | TATCCTACTT | ATCCCGATTC | ACCATTTCAG | GTCACCACTG | GATATCAGTT | 1380 |
| GCCTGTATAT | AATTATCAGC | CATTTCCTGC | TTATCCAAGT | TCACCATTTC | AGGTCACTGC | 1440 |
| TGGATATCAG | TTGCCTGTAT | ATAATTATCA | GGCATTTCCT | GCTTATCCAA | GTTCACCATT | 1500 |
| TCAGGTCACC | ACTGGATATC | AGTTGCCTGT | ATATAATTAT | CAGGCATTTC | CTGCTTATCC | 1560 |
| AAGTTCACCA | TTTCAGGTCA | CCACTGGATA | TCAGTTGCCT | GTATATAATT | ATCAGGCATT | 1620 |
| TCCTGCTTAT | CCAAGTTCAC | CATTTCAGGT | CACCACTGGA | TATCAGTTGC | CTGTATATAA | 1680 |
| TTATCAGGCA | TTTCCTGCTT | ATCCAAATTC | AGCAGTTCAG | GTCACCACTG | GATATCAGTT | 1740 |
| CCATGTATAC | AATTACCAGA | TGCCACCGCA | GTGCCCTGTT | GGGGAGCAAA | GGAGAAATCT | 1800 |
| GTGGACCGAA | GCATACAAAT | GGTGGTATCT | TGTCTGTTTA | ATCCAGAGA | | 1849 |

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AACGAAACAA ATCCATAGCC TTTG                                24

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CTCGCTCGCC CAGAACCGTA TCTACCAAAG CA                       32

( 2 ) INFORMATION FOR SEQ ID NO:18:

( i ) SEQUENCE CHARACTERISTICS:

(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:18:

GGGTTTTGCC TGCATACGTA ATTA 24

(2) INFORMATION FOR SEQ ID NO:19:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:19:

CCTAAAAGCA ATTCTAAACC TCCAG 25

(2) INFORMATION FOR SEQ ID NO:20:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:20:

CCACCTCATG GTAGTAAAAT TGTA 24

(2) INFORMATION FOR SEQ ID NO:21:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:21:

CTCTTATTTA TCTTATTGCT ACAACG 26

(2) INFORMATION FOR SEQ ID NO:22:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:22:

CAGTGATACA CTCGGACTTG TGTA 24

(2) INFORMATION FOR SEQ ID NO:23:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:23:

GTTATTTGAA AAGCTACACG GG 22

(2) INFORMATION FOR SEQ ID NO:24:

(i) SEQUENCE CHARACTERISTICS:
(A) LENGTH: 24 base pairs
(B) TYPE: nucleic acid (C) STRANDEDNESS: single
        (D) TOPOLOGY: linear (xi) SEQUENCE DESCRIPTION: SEQ ID NO:24:

TTAAGGGGAC AGTATTTCAA CTTC                                            24

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:25:

CCACATTTAA ACTGAGTACA GTCC                                            24

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

AACAAGTGAG TTCCACAGGG                                                 20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

GCAAAGCAGC ATTCAAAACA                                                 20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

CCTACCGCAT CGTGAATTTC                                                 20

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:29:

TCTGTATGTG GAGTACACAT GG                                              22

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear ( x i ) SEQUENCE DESCRIPTION: SEQ ID NO:30:

TGTTGTACGT AGAAAAAGGA TATTTTACC 29

( 2 ) INFORMATION FOR SEQ ID NO:31:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

ATATGGTAAA CCACTTTTTA AAATTGCCA 29

( 2 ) INFORMATION FOR SEQ ID NO:32:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ACAGTTTGAA ATGAAATTTT AAATGTGTT 29

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

TGACAAAGTG AGACCCTACT ACTA 24

( 2 ) INFORMATION FOR SEQ ID NO:34:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

AAGGATATTT TACCTTTGGT AAT 23

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GTGGAGCAGT GACCTGAAAT 20

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CCTTTGGTAA TATTTTGGTT ATAT 24

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:37:

ACTTGGATAA GCAGGAAATG GCTG 24

(2) INFORMATION FOR SEQ ID NO:38:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:38:

ACAGAATTTC AGTTGTATTT TTATTT 26

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:39:

ACCCTCCAAG ATATTAATTC TTTG 24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:40:

AATTAAAGGA CCCTTAAATT CATT 24

(2) INFORMATION FOR SEQ ID NO:41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:41:

CCTCTGAAAG ATTAATATAT GGTTCT 26

(2) INFORMATION FOR SEQ ID NO:42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:42:

GGACATAGTC CTGCTTAAGA AAAGTGG 27

( 2 ) INFORMATION FOR SEQ ID NO:43:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

ACGTGGTTCA GGAGGTCTAC TATTCTA                                                      27

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

ATGGGTGAGA AGCCTGATTG T                                                              21

( 2 ) INFORMATION FOR SEQ ID NO:45:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

TGGGAAAGCC TGAACTGCC                                                                19

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

GTAAGCCCCA GATACCCTCC                                                           20

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

AAATTGTTTG GAAAAGGACA CC                                                      22

( 2 ) INFORMATION FOR SEQ ID NO:48:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

ATAGTTAGTT TTGTGGTAAC AT                                                      22

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

CATAGCCTCT ATGCAGATGG G            21

( 2 ) INFORMATION FOR SEQ ID NO:50:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

ATTGATGTGT TGCCCCAAT            19

( 2 ) INFORMATION FOR SEQ ID NO:51:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

AGAGTGAACT TTAAATCCCA GCC          23

( 2 ) INFORMATION FOR SEQ ID NO:52:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GACTCTACCA CTTGGGCTCA ATTT         24

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

AGATGTACCC AAGGCCACTG           20

( 2 ) INFORMATION FOR SEQ ID NO:54:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AGTTAGTAAG CCCCAGTTAT CCTCC        25

( 2 ) INFORMATION FOR SEQ ID NO:55:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:55:

TTTGGAAAAG GACACCTTAT TAGCCA 26

( 2 ) INFORMATION FOR SEQ ID NO:56:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:56:

CCCCATCGGT AAACCAAATC A 21

( 2 ) INFORMATION FOR SEQ ID NO:57:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:57:

CCCATTGAAG TTTCAAGGTG TCA 23

( 2 ) INFORMATION FOR SEQ ID NO:58:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:58:

CATTCATCTT CCCTTTTGAA GG 22

( 2 ) INFORMATION FOR SEQ ID NO:59:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:59:

ATGCAAGTCG CAGGAAATCT 20

( 2 ) INFORMATION FOR SEQ ID NO:60:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:60:

TCAAATAGCA GCAATTTAAT AT 22

( 2 ) INFORMATION FOR SEQ ID NO:61:

( i ) SEQUENCE CHARACTERISTICS:
    ( A ) LENGTH: 19 base pairs (B) TYPE: nucleic acid
(C) STRANDEDNESS: single
(D) TOPOLOGY: linear (xi) SEQUENCE DESCRIPTION: SEQ ID NO:61:

GCACCTGAAG AGCTGCTTG 19

(2) INFORMATION FOR SEQ ID NO:62:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:62:

ACACAGTAGC AGCGGGAGTT 20

(2) INFORMATION FOR SEQ ID NO:63:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:63:

TCTGCCACTA AACTGTAAGC TCC 23

(2) INFORMATION FOR SEQ ID NO:64:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:64:

GTTTCTTCAT AAGCAACCAA ATTG 24

(2) INFORMATION FOR SEQ ID NO:65:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:65:

CAGATTATGC CACTGCCCTT 20

(2) INFORMATION FOR SEQ ID NO:66:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:66:

TTACTTCCTT AAGTCAAAGC GG 22

(2) INFORMATION FOR SEQ ID NO:67:

(i) SEQUENCE CHARACTERISTICS:
(A) LENGTH: 21 base pairs
(B) TYPE: nucleic acid
(C) STRANDEDNESS: single ( D ) TOPOLOGY: linear ( x i ) SEQUENCE DESCRIPTION: SEQ ID NO:67:

CTGAGACAGC AAGACCAATC C                                                                                  21

( 2 ) INFORMATION FOR SEQ ID NO:68:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:68:

CTGGACAAAG CCTTGGAAAA                                                                                    20

( 2 ) INFORMATION FOR SEQ ID NO:69:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:69:

CTGCATGTCA ATTGTGGGAC                                                                                    20

( 2 ) INFORMATION FOR SEQ ID NO:70:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:70:

CATTGGCATG AATGTGTATT C                                                                                  21

( 2 ) INFORMATION FOR SEQ ID NO:71:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:71:

CTCTGGGACA AGTGTTCCTT                                                                                    20

( 2 ) INFORMATION FOR SEQ ID NO:72:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:72:

GACAAAGGGC TGATGATTTA                                                                                    20

( 2 ) INFORMATION FOR SEQ ID NO:73:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:73:

CATCACCTTT ACTTTTTAAA TGG    23

( 2 ) INFORMATION FOR SEQ ID NO:74:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

GGGTGTTACC AGAAGGCAAA    20

( 2 ) INFORMATION FOR SEQ ID NO:75:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

GAACCGTATC TACCAAAGCA GC    22

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

GTTACAGGAT TCGGCGTGAT    20

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

CTCGTCATGT GCAGCCAC    18

( 2 ) INFORMATION FOR SEQ ID NO:78:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

AGGTTGTTTG GCCTTGAGC    19

( 2 ) INFORMATION FOR SEQ ID NO:79:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

TCTATGATCT GTACCCGGTG C    21

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

AGCTCACTGC AAGCAACAGA    20

( 2 ) INFORMATION FOR SEQ ID NO:81:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

CCACCATCCC CCTTCTTC    18

( 2 ) INFORMATION FOR SEQ ID NO:82:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

GAATGTGTAT TCAAGGACTT CTCG    24

( 2 ) INFORMATION FOR SEQ ID NO:83:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

TACTTCCTTC GGGGCCTCT    19

( 2 ) INFORMATION FOR SEQ ID NO:84:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

CTCTGGGACA AGTGTTCCTT G    21

( 2 ) INFORMATION FOR SEQ ID NO:85:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CATTGGCATG AATGTGTATT CA    22

( 2 ) INFORMATION FOR SEQ ID NO:86:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

GGTGAGTCAA ATTAGTCAAT GTCC        24

( 2 ) INFORMATION FOR SEQ ID NO:87:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

CCTTACCACA GGACAGAGGG        20

( 2 ) INFORMATION FOR SEQ ID NO:88:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

GGTCTTTAAA AGGTGAGTCA AATT        24

( 2 ) INFORMATION FOR SEQ ID NO:89:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

AGACAGAGGG AACTTCAAGA CC        22

( 2 ) INFORMATION FOR SEQ ID NO:90:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

GACACTCTCG AGACATCACC GTCC        24

( 2 ) INFORMATION FOR SEQ ID NO:91:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

GATCGGACGG TGATGTCTCG AGAGTG        26

( 2 ) INFORMATION FOR SEQ ID NO:92:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:92:

AACGAAACAA ATCCATAGCC TTTG 24

( 2 ) INFORMATION FOR SEQ ID NO:93:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:93:

CTCGCTCGCC CAGAACCGTA TCTACCAAAG CA 32

( 2 ) INFORMATION FOR SEQ ID NO:94:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:94:

AATTCTTGCG CCTTAAACCA AC 22

( 2 ) INFORMATION FOR SEQ ID NO:95:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:95:

GTTGGTTTAA GGCGCAAG 18

( 2 ) INFORMATION FOR SEQ ID NO:96:

( i ) SEQUENCE CHARACTERISTICS:
( A ) LENGTH: 366 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:96:

```
Met Ser Ala Ala Asn Pro Glu Thr Pro Asn Ser Thr Ile Ser Arg Glu
 1               5                  10                  15

Ala Ser Thr Gln Ser Ser Ser Ala Ala Ala Ser Gln Gly Trp Val Leu
            20                  25                  30

Pro Glu Gly Lys Ile Val Pro Asn Thr Val Phe Val Gly Gly Ile Asp
        35                  40                  45

Ala Arg Met Asp Glu Thr Glu Ile Gly Ser Cys Phe Gly Arg Tyr Gly
    50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95
```

```
Val  Gly  Ser  Gln  Ile  His  Phe  His  Gly  Lys  Lys  Leu  Lys  Leu  Gly  Pro
               100                           105                      110

Ala  Ile  Arg  Lys  Gln  Lys  Leu  Cys  Ala  Arg  His  Val  Gln  Pro  Arg  Pro
          115                      120                      125

Leu  Val  Val  Asn  Pro  Pro  Pro  Pro  Gln  Phe  Gln  Asn  Val  Trp  Arg
     130                 135                      140

Asn  Pro  Asn  Thr  Glu  Thr  Tyr  Leu  Gln  Pro  Gln  Ile  Thr  Pro  Asn  Pro
145                      150                      155                           160

Val  Thr  Gln  His  Val  Gln  Ala  Tyr  Ser  Ala  Tyr  Pro  His  Ser  Pro  Gly
               165                           170                      175

Gln  Asn  Ile  Thr  Gly  Cys  Gln  Leu  Leu  Val  Tyr  Asn  Tyr  Gln  Glu  Tyr
               180                      185                      190

Pro  Thr  Tyr  Pro  Asp  Ser  Pro  Phe  Gln  Val  Thr  Thr  Gly  Tyr  Gln  Leu
          195                      200                      205

Pro  Val  Tyr  Asn  Tyr  Gln  Pro  Phe  Pro  Ala  Tyr  Pro  Ser  Ser  Pro  Phe
     210                      215                      220

Gln  Val  Thr  Ala  Gly  Tyr  Gln  Leu  Pro  Val  Tyr  Asn  Tyr  Gln  Ala  Phe
225                           230                      235                     240

Pro  Ala  Thr  Pro  Ser  Ser  Pro  Phe  Gln  Val  Thr  Thr  Gly  Tyr  Gln  Leu
                    245                      250                      255

Pro  Val  Tyr  Asn  Tyr  Gln  Ala  Phe  Pro  Ala  Tyr  Pro  Ser  Ser  Pro  Phe
               260                      265                      270

Gln  Val  Thr  Thr  Gly  Tyr  Gln  Leu  Pro  Val  Tyr  Asn  Tyr  Gln  Ala  Phe
               275                      280                      285

Pro  Ala  Tyr  Pro  Ser  Ser  Pro  Phe  Gln  Val  Thr  Thr  Gly  Tyr  Gln  Leu
     290                      295                      300

Pro  Val  Tyr  Asn  Tyr  Gln  Ala  Phe  Pro  Ala  Tyr  Pro  Asn  Ser  Ala  Val
305                      310                      315                          320

Gln  Val  Thr  Thr  Gly  Tyr  Gln  Phe  His  Val  Tyr  Asn  Tyr  Gln  Met  Pro
               325                      330                      335

Pro  Gln  Cys  Pro  Val  Gly  Glu  Gln  Arg  Arg  Asn  Leu  Trp  Thr  Glu  Ala
               340                      345                      350

Tyr  Lys  Trp  Trp  Tyr  Leu  Val  Cys  Leu  Ile  Gln  Arg  Arg  Asp
          355                      360                      365
```